United States Patent [19]
Babson et al.

[11] Patent Number: 5,885,529
[45] Date of Patent: Mar. 23, 1999

[54] AUTOMATED IMMUNOASSAY ANALYZER

[75] Inventors: Arthur L. Babson, Chester; Thomas Palmieri, Paramus, both of N.J.; Anthony P. Montalbano, Shelter Island Heights, N.Y.; Chris P. Montalbano; Greg A. Montalbano, both of Great Neck, N.Y.; Eric C. Fleischer, Rockville Centre, N.Y.

[73] Assignee: DPC Cirrus, Inc., Randolph, N.J.

[21] Appl. No.: 672,654

[22] Filed: Jun. 28, 1996

[51] Int. Cl.[6] .......................... G01N 35/02; G01N 35/10
[52] U.S. Cl. ............................ 422/65; 422/63; 422/64; 422/67; 436/43; 436/47; 436/48; 436/49; 436/165; 436/177; 436/179; 436/180; 220/253; 220/255; 220/348; 134/150; 134/157; 221/264; 221/266
[58] Field of Search .................. 422/63–65, 67, 422/68.1, 81, 100, 101, 102, 103, 104; 436/43, 47, 48, 49, 54, 174, 177, 179, 180; 206/569; 220/253, 255, 264, 281, 348; 222/518, 559, 482; 215/315; 221/264, 266; 134/150, 157

[56] References Cited

U.S. PATENT DOCUMENTS

| | | | |
|---|---|---|---|
| 1,162,791 | 12/1915 | Lubas | 220/253 |
| 3,118,577 | 1/1964 | Estabrook | 215/315 |
| 3,151,073 | 9/1964 | Anthon | 422/72 |
| 3,169,679 | 2/1965 | Hunter | 220/253 |
| 3,392,060 | 7/1968 | Favre | 220/253 |
| 3,432,149 | 3/1969 | Stahlberg et al. | 366/202 |
| 3,679,129 | 7/1972 | Livshitz et al. | 233/26 |
| 3,726,144 | 4/1973 | Klein | 422/100 |
| 4,053,284 | 10/1977 | Posch | 23/259 |
| 4,101,284 | 7/1978 | Difiglio et al. | 23/259 |
| 4,323,537 | 4/1982 | Mody | 422/63 |
| 4,405,060 | 9/1983 | Hsei | 221/135 |
| 4,415,098 | 11/1983 | Haas | 221/202 |
| 4,492,316 | 1/1985 | Emms | 221/202 |
| 4,517,851 | 5/1985 | Tice | 73/864.91 |
| 4,534,465 | 8/1985 | Rothermal et al. | 206/443 |
| 4,673,813 | 6/1987 | Sanchez | 220/255 |
| 4,706,842 | 11/1987 | Guadagnino | 221/14 |
| 4,718,570 | 1/1988 | Diener | 220/255 |
| 4,731,225 | 3/1988 | Wakatake | 422/65 |
| 4,767,600 | 8/1988 | Vicario | 422/65 |
| 4,816,418 | 3/1989 | Mack et al. | 436/518 |
| 4,879,242 | 11/1989 | Tsukioka | 436/54 |
| 4,895,453 | 1/1990 | Devlin et al. | 366/219 |
| 4,943,164 | 7/1990 | Ohishi | 366/149 |
| 4,944,924 | 7/1990 | Mawhirt et al. | 422/104 |
| 4,980,292 | 12/1990 | Elbert et al. | 435/289 |

(List continued on next page.)

OTHER PUBLICATIONS

Trade Brochure, entitled "PK310 Fully Automated Enzyme Analyser", a publication of Olympus Biomedical Products Div., Wendenstrasse 14–16, 2 Hamburg 1, Germany, 15 pages, undated.

Primary Examiner—Long V. Le
Attorney, Agent, or Firm—Whitham, Curtis & Whitham

[57] ABSTRACT

An improved automated immunoassay analyzer including a high throughput automated immunoassay system which can perform high volume testing on a broad range of analytes while selecting from among a diverse set of immunoassays for any given sample. The immunoanalyzer has the capacity to perform a wide range of different types of immunoassays by facile storage and automated combination aboard the instrument among a wide variety of different types of reagents and heterogenous immunoassay beads stored on-board the instrument. The automated design allows reduced user interface (e.g., tests are performed automatically from computer input) including the ability to order, perform and reassay tests reflexively based on test results without operator intervention. Further, the inventive analyzer is not sample tube specific; that is, an instrument that can accept sample tube sizes within a broad size range. The inventive automated immunoassay analyzer also provides a re-useable sample dilution well, and a high speed bead washing station that eliminates the need for assay tubes having integral, waste fluid collection chambers.

17 Claims, 20 Drawing Sheets

U.S. PATENT DOCUMENTS

| | | | |
|---|---|---|---|
| 5,051,238 | 9/1991 | Umetsu et al. | 422/64 |
| 5,104,231 | 4/1992 | Collier et al. | 366/208 |
| 5,128,105 | 7/1992 | Berthold et al. | 422/104 |
| 5,137,693 | 8/1992 | Mawhirt | 422/104 |
| 5,158,895 | 10/1992 | Ashihara et al. | 436/526 |
| 5,175,086 | 12/1992 | Takekawa et al. | 435/7.92 |
| 5,178,834 | 1/1993 | Kagayama et al. | 422/65 |
| 5,183,638 | 2/1993 | Wakatake | 422/64 |
| 5,186,339 | 2/1993 | Heissler | 211/74 |
| 5,215,714 | 6/1993 | Okada et al. | 422/64 |
| 5,221,519 | 6/1993 | Wuerschum | 422/65 |
| 5,248,056 | 9/1993 | Shaw | 220/331 |
| 5,282,543 | 2/1994 | Picozza et al. | 220/255 |
| 5,316,726 | 5/1994 | Babson et al. | 422/65 |
| 5,350,564 | 9/1994 | Mazza et al. | 422/63 |
| 5,372,786 | 12/1994 | Iles | 422/104 |
| 5,378,433 | 1/1995 | Duckett et al. | 422/100 |
| 5,380,487 | 1/1995 | Choperena et al. | 422/63 |
| 5,397,542 | 3/1995 | Nelms et al. | 422/104 |
| 5,439,645 | 8/1995 | Saralegui et al. | 422/64 |
| 5,542,575 | 8/1996 | Stark et al. | 220/256 |
| 5,578,494 | 11/1996 | Clark et al. | 436/54 |

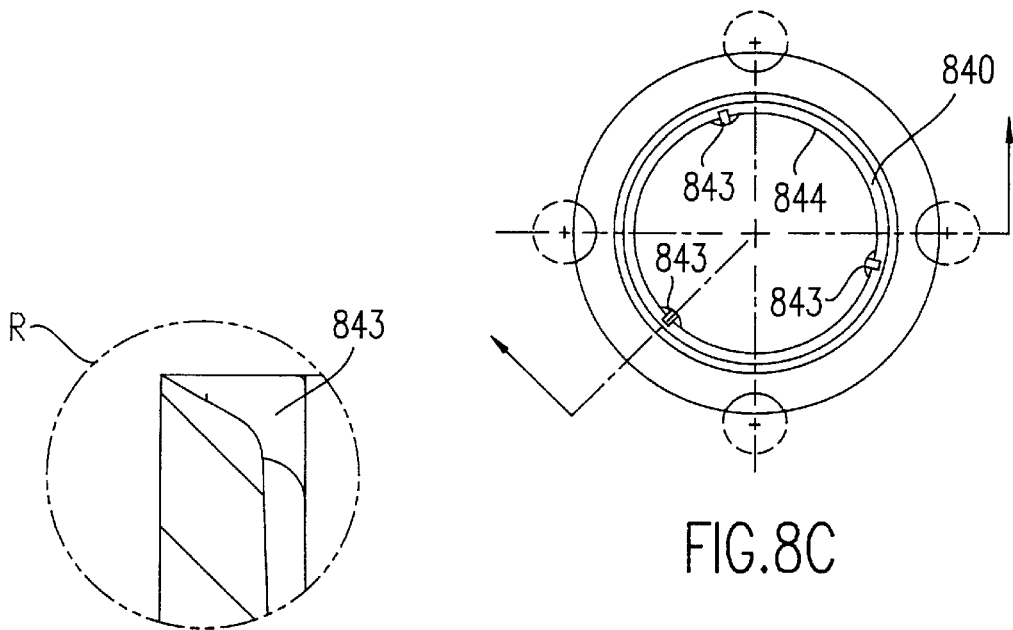
FIG.8C
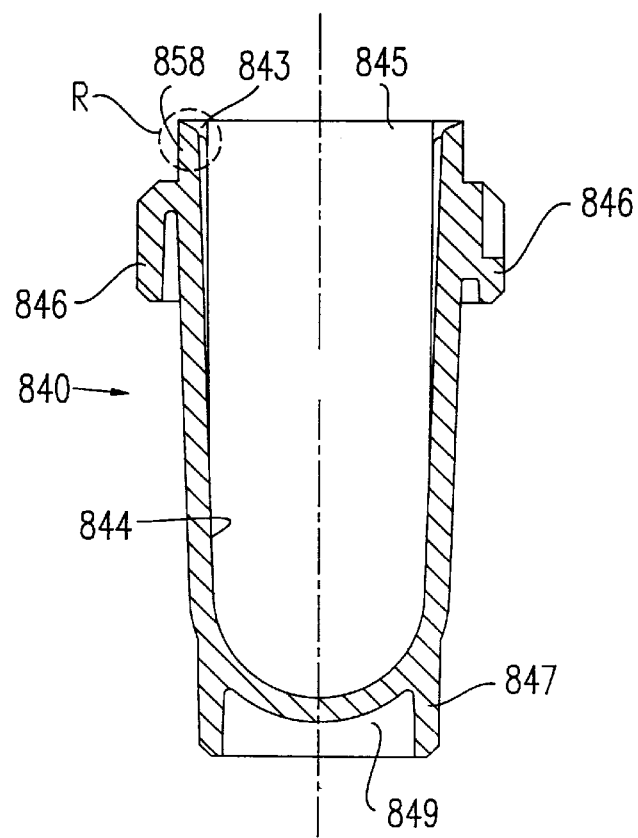
FIG.8D
FIG.8B

AUTOMATED IMMUNOASSAY ANALYZER

BACKGROUND OF THE INVENTION

1. Field of the Invention

The present invention is generally relates to an automated immunoassay analyzer and, more particularly, to a high throughput automated immunoassay analyzer which permits high volume assay of a broad range of analytes in bodily fluids.

2. Description of the Prior Art

An immunoassay is a well known laboratory method used to determine the amount of an analyte in a sample such as plasma or urine. It is based on the interaction of antibodies with antigens, and because of the degree of selectivity for the analyte (either antigen or antibody), an immunoassay can be used to quantitatively determine very low concentrations of drugs, hormones, polypeptides, or other analyte compounds found in a test sample. For many years, immunoassays were performed by hand by trained laboratory technicians.

More recently, many companies have begun producing automated immunoassay analyzers. Automating the immunoassay procedures can be onerous because of the large number of steps needed to be executed. For example, in a conventional scheme, a sample is mixed with a reagent and a solid support having a bound antigen or antibody, the sample is incubated such that the corresponding antigen or antibody in the sample and a labeled antigen or antibody provided in the reagent can be bound to the antigen or antibody on the solid support, then the solid support is thoroughly washed and the label (fluorescent, radioactive, chemiluminescent, or the like) is detected by an appropriate mechanism, and finally the analyte of interest (antigen or antibody) is quantified from the detected label.

Most of today's automated immunoassay analyzers are designed for "walk away" operation, where the technician loads sample containing tubes onto a carousel and presses a start button. Thereafter, the automated immunoassay analyzer mixes appropriate reagents (often stored aboard the analyzer) with the sample, performs incubating and washing operations, detects the label, and computes the quantity of analyte in the sample from the detected label and stored calibration curves. The entire operation is typically done under computer control, and in some automated immunoassay analyzers, bar coding is used to identify the sample under test. The results of the immunoassays are typically output onto computer paper for inspection by the technician, or they can be monitored and displayed in real time as described in U.S. Pat. No. 5,316,726 to Babson et al. The immunoassay instrument described in U.S. Pat. No. 5,316,726 employs assay tubes that are preloaded with the immunoassay beads before the tubes are placed on the instrument.

Another automated immunoassay instrument is described in a trade brochure published by Olympus (Biomedical Products Division), Wendenstrasse 14-16, 2 Hamburg 1, Germany, describing an automated enzyme immunoassay analyzer under model no. "PK310", which is a sequential batch-processing system using a reaction disc containing U-shaped reaction tubes. A bead storage unit is included on-board the instrument for loading of assay tubes on the instrument comprising a plurality of bead cassettes mounted on a carousel. Each bead cassette stores a plurality of solid support beads as a column on a spiral track, where the beads exit the bottom of the spiral track into an open-air holding receptacle adjoining the outside of the base of the bead pack. The dispensed beads are picked up by a vacuum-operated bead transport for feeding into a U-shaped reaction tube.

With respect to hospital and clinical laboratories performing large numbers of tests per month, e.g., at least 5,000 tests per month, immunoassay systems are demanded which can handle high volume LIS based test ordering while retaining the capability of accepting test orders and any prioritizations directly from an operator.

SUMMARY OF THE INVENTION

It is an object of this invention to provide an improved automated immunoassay analyzer.

It is another object of the invention to provide a high throughput automated immunoassay system which can perform high volume testing on a broad range of analytes while selecting from among a diverse set of immunoassays.

It is a further object of the invention to provide capacity to perform a wide range of different types of immunoassays by storage and automated combination aboard the instrument among a wide variety of different types of reagents and immunoassay beads stored on-board the instrument.

It is yet another object to provide an automated design which allows reduced user interface (e.g., tests are performed automatically from computer input) including the ability to order, perform and reassay tests reflexively based on test results without operator intervention.

It is a another object of the invention to provide an instrument that is not sample tube specific; that is, an instrument that can accept sample tube sizes within a broad size range.

It is yet another object of the invention to provide a re-useable sample dilution well and a re-useable bead wash station to reduce manual labor requirements and avoid the waste of single-use disposable mixing cups.

According to the invention, an improved automated immunoassay analyzer is provided. The inventive automated immunoassay analyzer allows for loading and specimen extraction from the original sample tubes loaded directly on-board the instrument, wherein a wide variety of different types of tests can be performed on any given sample by the provision of a bead pack carousel and a reagent carousel that can be computer controlled to allow automated picking, choosing and combining among the various beads and reagents with a sample on-board the instrument to conduct the test(s) desired for each sample. The analyzer has a computer control which controls the selection of reagents and beads for performing a variety of immunoassays on a number of different samples which are loaded into the analyzer. In addition, the computer controls the timing of incubation, mixing, washing, and detection operations.

BRIEF DESCRIPTION OF THE DRAWINGS

The foregoing and other objects, aspects and advantages will be better understood from the following detailed description of the preferred embodiments of the invention with reference to the drawings, in which.

Figure 6:
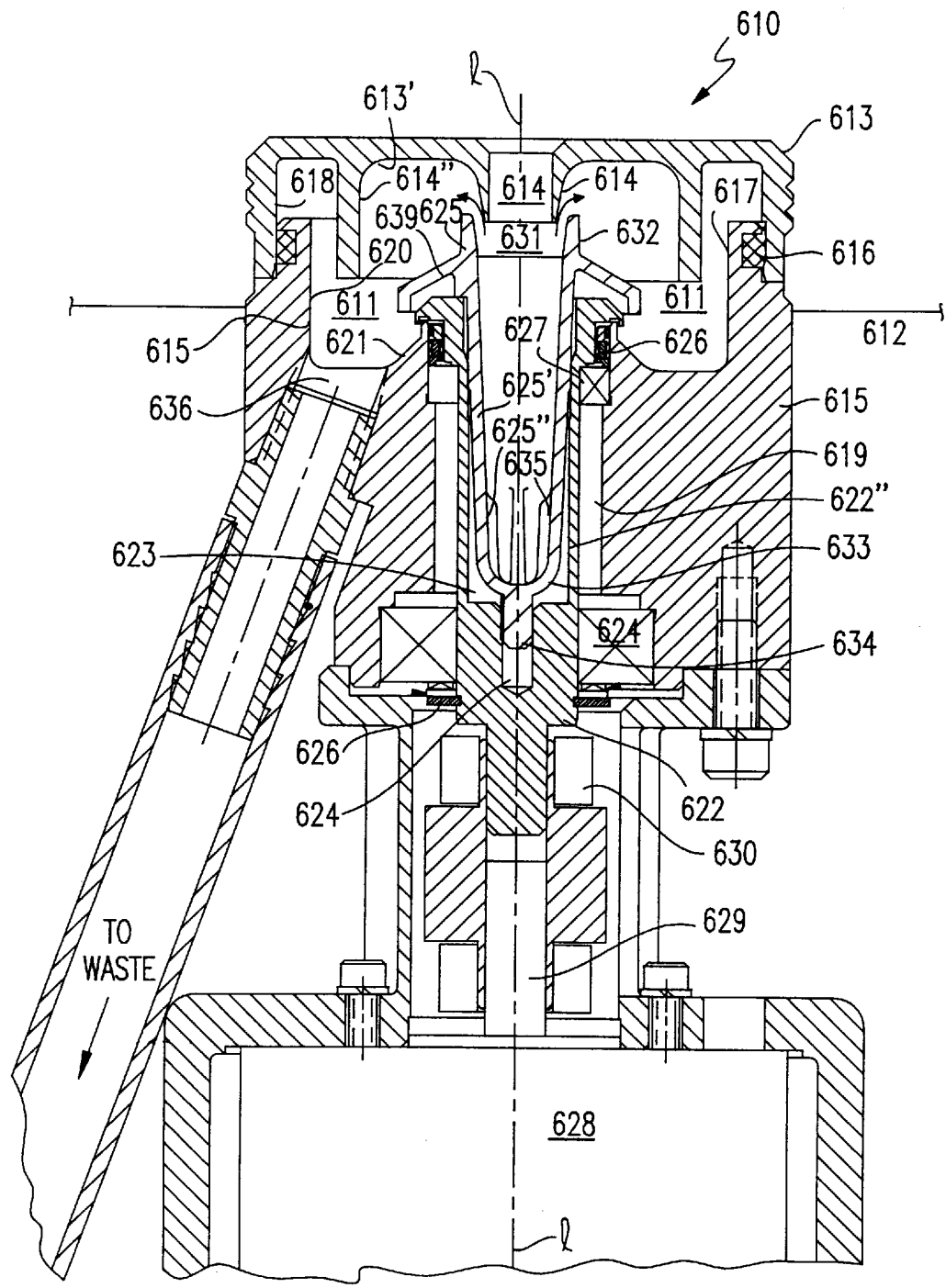
Figure 7C:
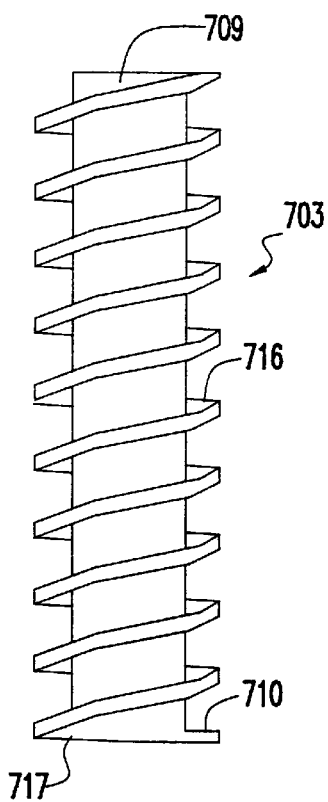
Figure 7A:
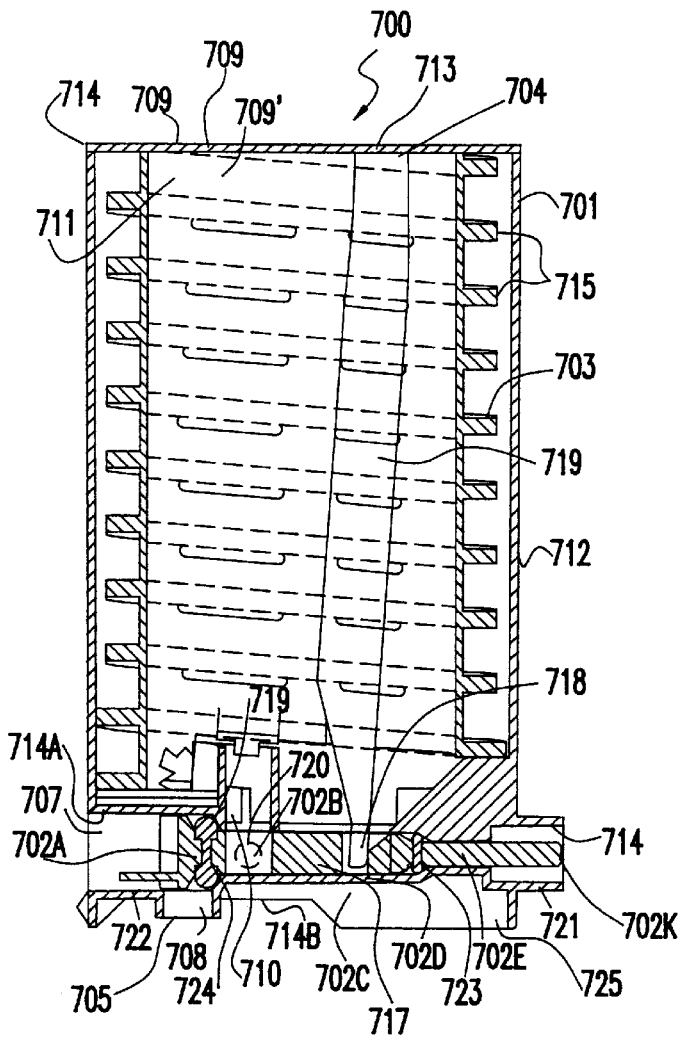
Figure 7D:
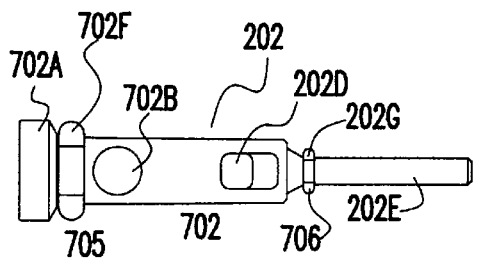
Figure 7E:
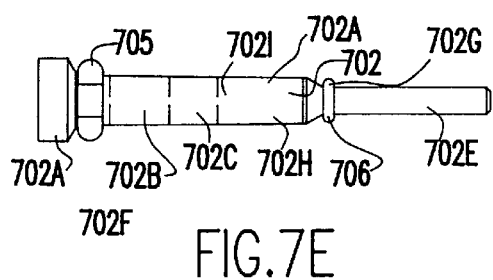
Figure 7B:
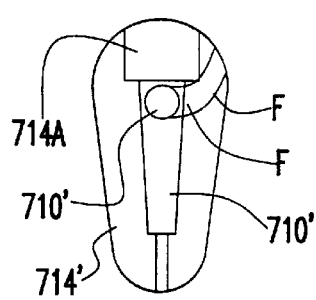
Figure 7F:
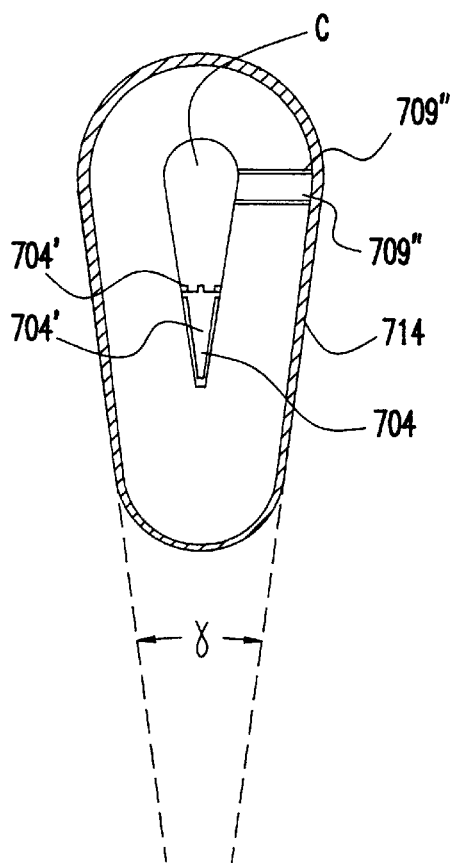
Figure 7G:
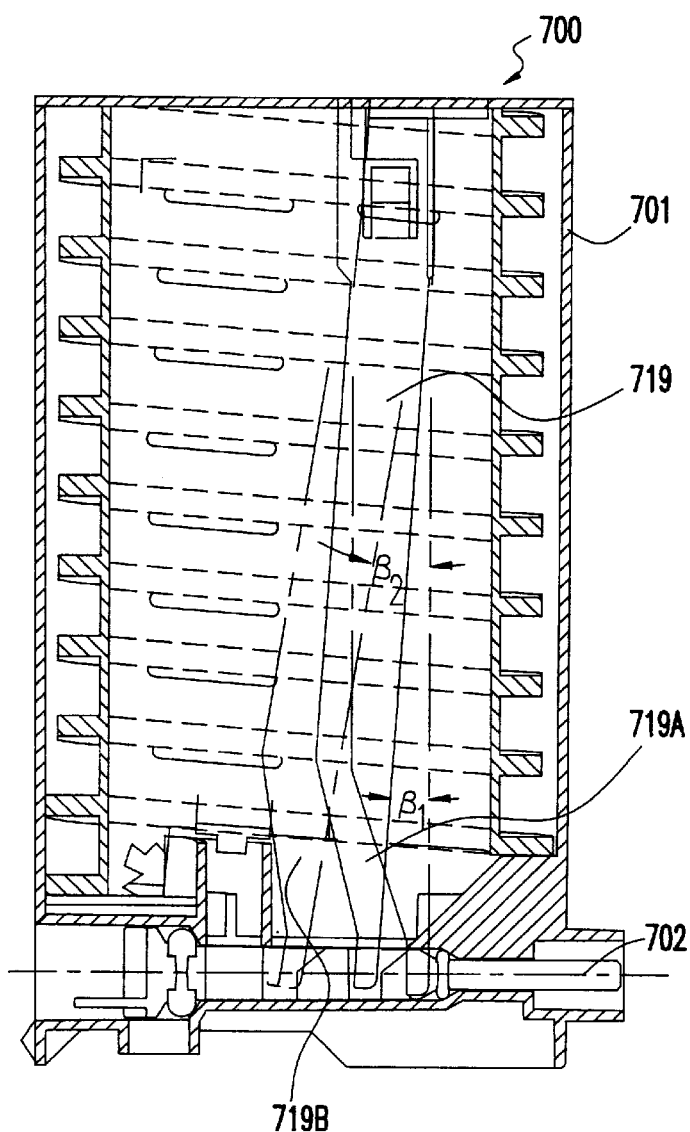
Figure 8A:
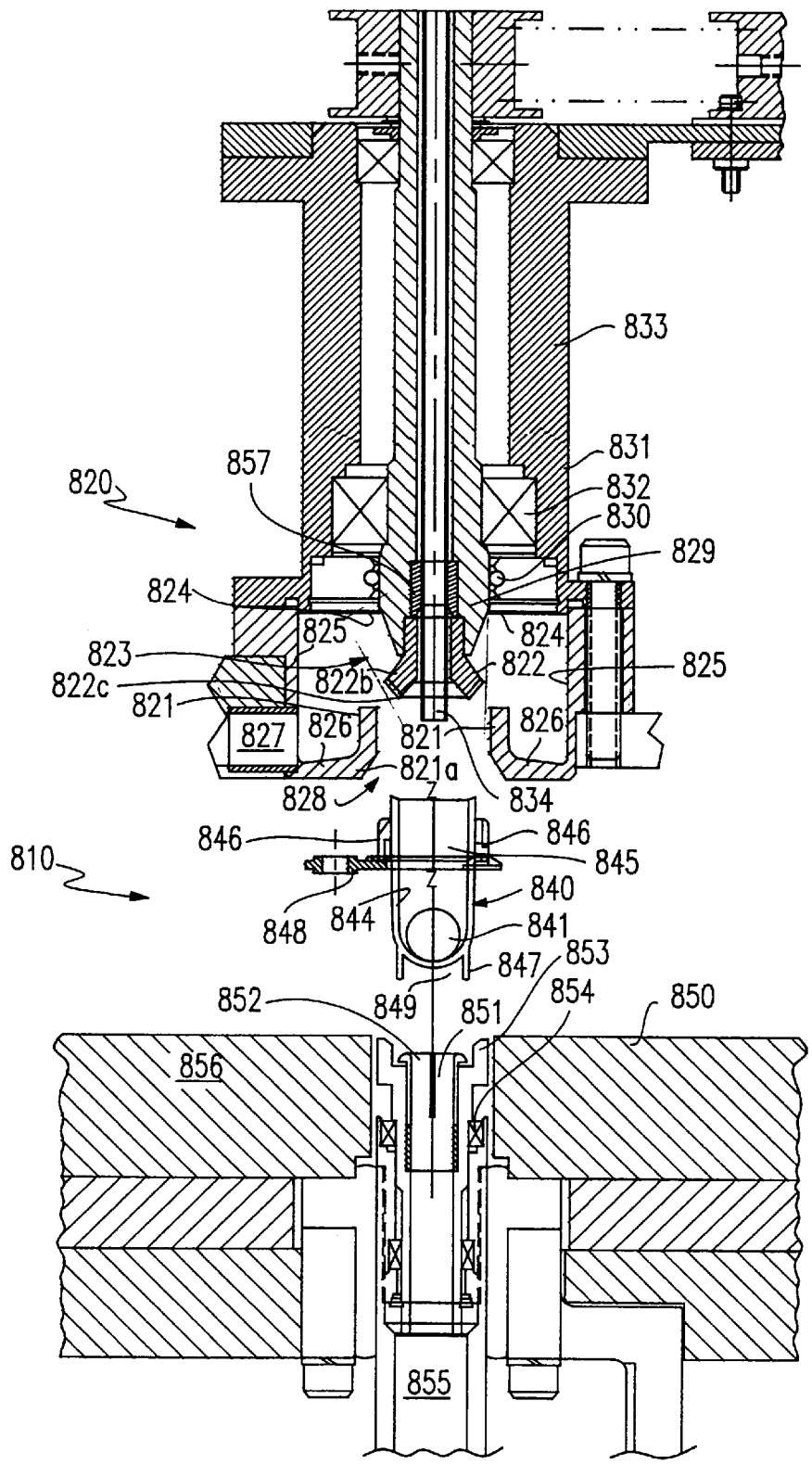
Figure 8E:
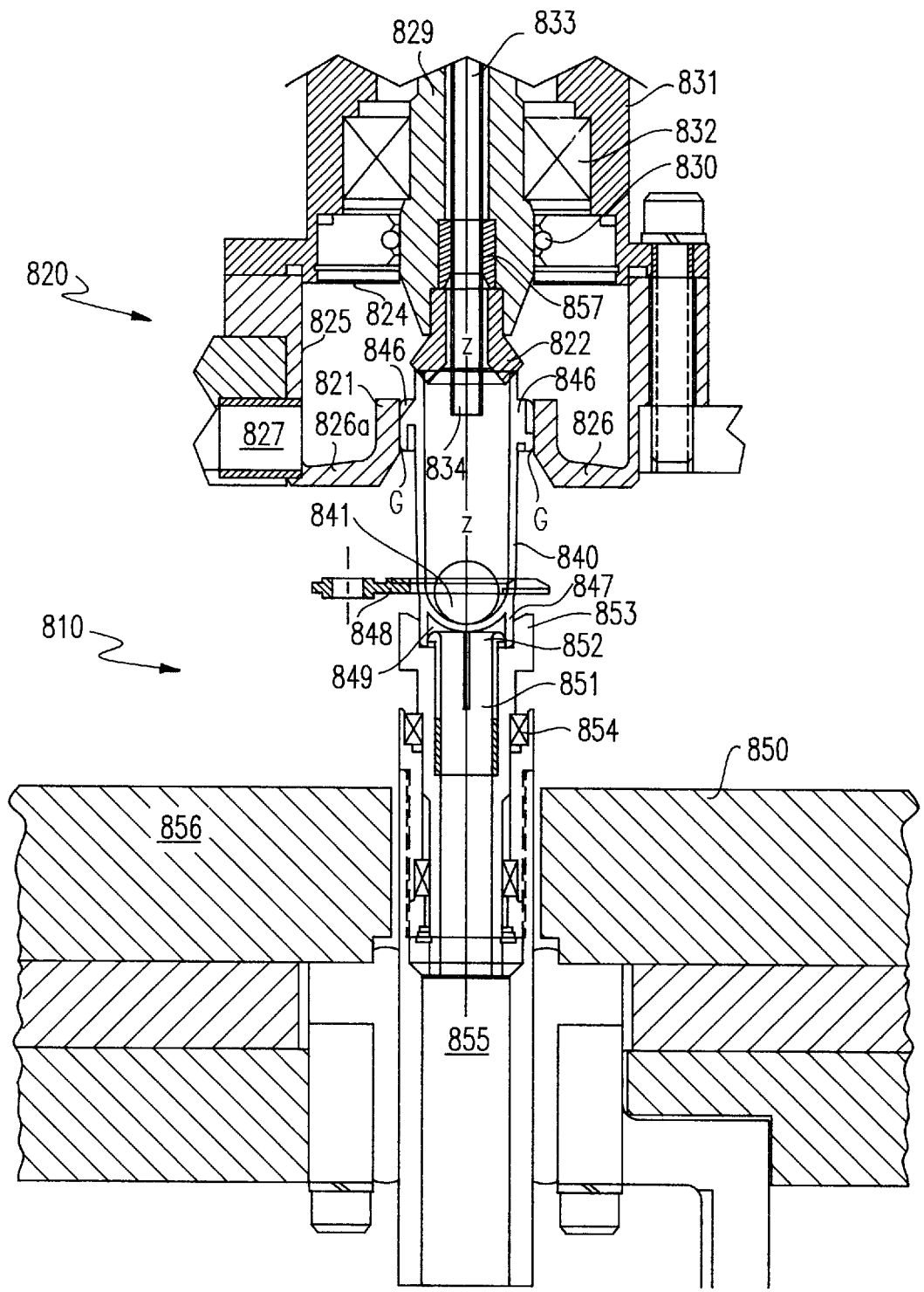
Figure 8F:
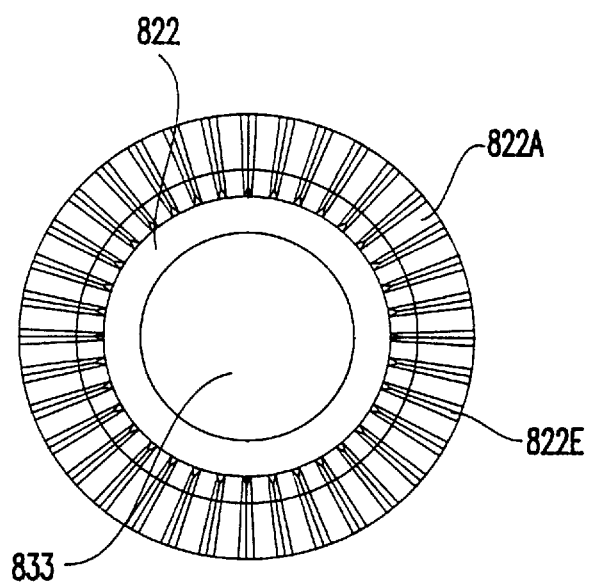
Figure 8G:
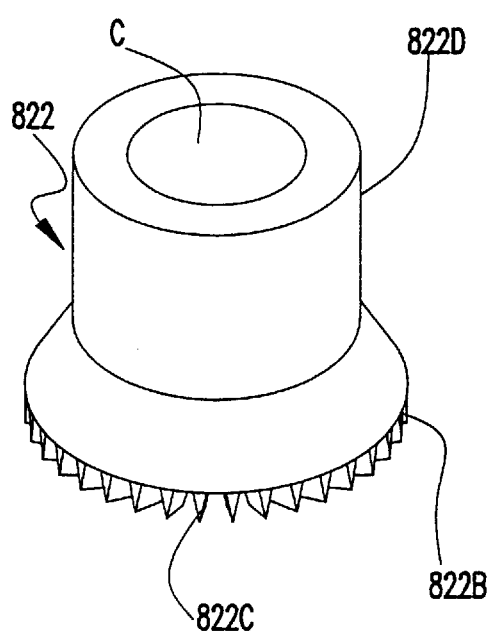

The FIG. 6 is a cross-sectional view of a sample dilution well system of the invention;

FIG. 7A is a cross-sectional side view of a dispenser device of the invention;

FIG. 7B is a cross-sectional top view of the bead chamber and its plunger chamber from the perspective of direction B7—B7 indicated in FIG. 7A;

FIG. 7C is a fragmentary side perspective view of the bead track component of the dispenser device of FIG. 7A;

FIG. 7D is a fragmentary top perspective view of the plunger component of the dispenser device of FIG. 7A;

FIG. 7E is a fragmentary side perspective view of the plunger component of the dispenser device of FIG. 7A;

FIG. 7F is a cross-sectional top view of the bead chamber, bead track, and plunger biasing spring from the perspective of direction C7—C7 indicated in FIG. 7A;

FIG. 7G is a cross-sectional side view of a dispenser device of the invention showing the at rest and dispensing modes of the device;

FIG. 8A is a cross-sectional side view of a tube wash system of the invention in a nonengaged status with an assay tube;

FIG. 8B is an enlarged fragmentary cross-sectional side view of the assay tube used in the tube wash system of FIG. 8A;

FIG. 8C is a top view of the assay tube of FIG. 8B;

FIG. 8D is an enlarged view of encircled area R in FIG. 8B;

FIG. 8E is a cross-sectional side view of a tube wash system of the invention in an engaged status with an assay tube;

FIG. 8F is an enlarged bottom view of a drive chuck used in a high speed spinning station of a tube washing station of the invention;

FIG. 8G is a top perspective view of the drive chuck of FIG. 8F; and

Figure 8H:
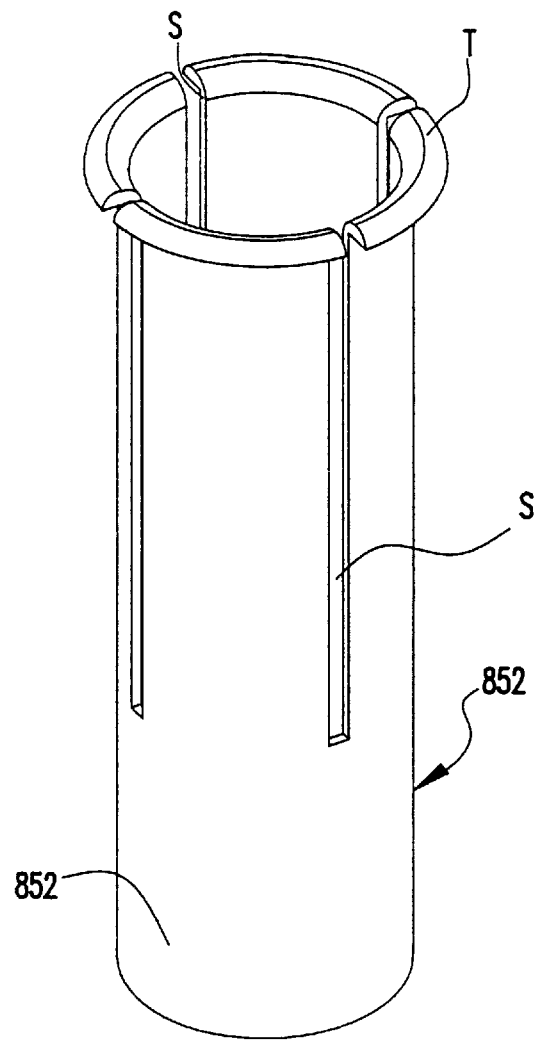

FIG. 8H is a top perspective view of a tube holder used to support the bottom of a test tube during its washing in a tube washing station of the invention.

DETAILED DESCRIPTION OF THE PREFERRED EMBODIMENTS OF THE INVENTION

The analytical instrument of this invention produces reportable assay results through the processing of specimens and various other components of the chemistry system. This processing involves the control and timing of various internal operations as well as the acquisition and processing of data generated internally or through interaction with an external computer system such as LIS. The analytic instrument is an integrated electromechanical apparatus which processes specimens in order to generate test results. It is comprised of all the mechanical hardware, electronic hardware and software required to perform immunoassays described herein. It is anticipated that many different constituents in the sample can be tested by immunoassay by the inventive instrument depending on the selection of the biomaterial bound to the inert support (e.g., bead) in the assay tube.

Figure 1:
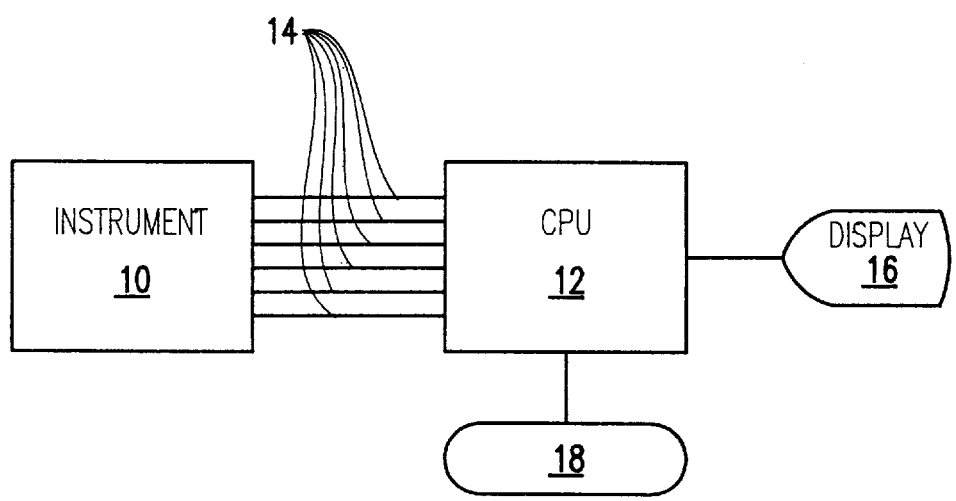
FIG. 1 is a generalized block diagram of the automated immunoassay analyzer.

Referring now to the drawings, and more particularly to FIG. 1, there is shown a generalized block diagram of the automated immunoassay analyzer wherein the instrument 10, described in greater detail elsewhere herein, that actually performs the immunoassays on multiple samples is connected to a computer 12 via data communication lines 14. The data communication lines 14 are used to supply information from the instrument 10 to computer 12 such as bar coded information on sample tubes, reagent supply packs, and bead supply packs on-board the instrument as well as photon counts measured by a photomultiplier tube. The instrument 10 is preferably operated under the direction of on-board microprocessors (not shown). The operations and layout of the instrument 10 and computer 12 are discussed in more detail in conjunction with FIGS. 2A,B and 3. The computer 12 is connected to a display 16 which presents the operator with a status report on all tests ordered and operations occurring within the instrument 10. A display 16 is provided to display operator commands and data collected from the instrument. A keyboard 18 is provided for the operator to allow input of patient information associated with, and tests desired for, their test samples or to perform other analysis and control functions.

Figure 2A:
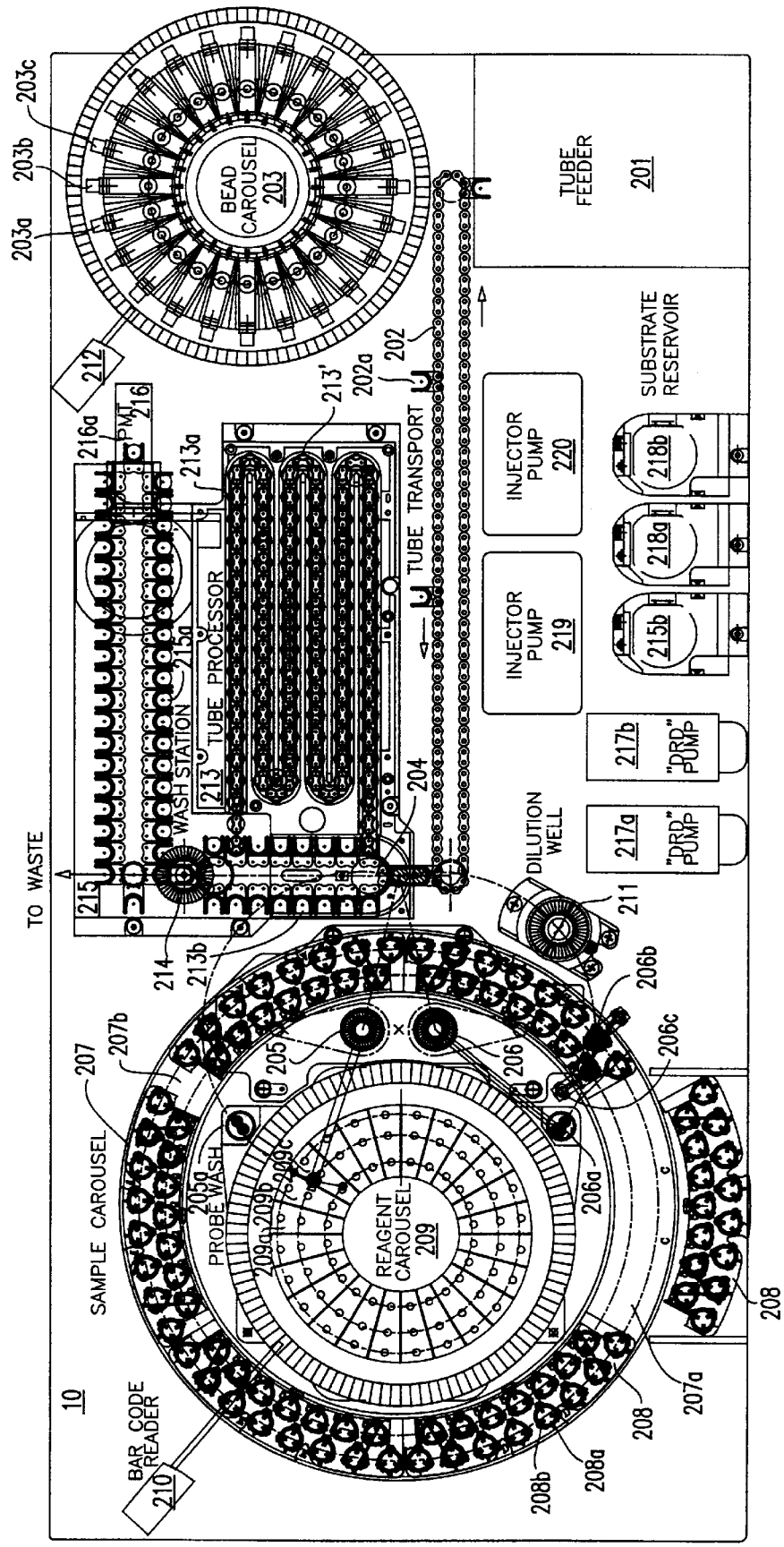
FIG. 2A is a plan view diagram of the flow path of samples and assays through the automated immunoassay analyzer.

FIG. 2A shows the internal details of the instrument 10. The basic layout and functions of each subsystem of the instrument are summarized below with more detailed descriptions of several of the subsystems provided later herein.

A reaction tube feeder/dispenser 201 is a device which accepts reaction tubes 840 (see FIGS. 8A–C) in bulk in a hopper, orients them and delivers them individually to the reaction tube load chain 202, such as via an elevator ladder means (not shown). The reaction tubes 840 are disposable unit dose devices used by the instrument to contain beads and reagents during processing. They serve to contain sample/reagent mixtures during sample pre-treatment operations when required. As such, all transportation, incubation, separation and signal generation steps for all tests are carried out in these reaction tubes. The reaction tube loader chain 202 is a chain having arcuate, horizontally oriented arms 202a that accept reaction tubes 840 from the reaction tube dispenser 201, supporting the tubes 840 at flanges 846, such as seen in FIG. 8B, integrally formed at the top of the reaction tubes 840. The chain 202 transports the reaction tubes 840 first under a tube outlet where beads drop by gravity after being dispensed from the bead dispenser and carousel 203.

The bead carousel 203 supports a plurality of bead packs 203a, 203b, 203c, and so forth, each capable of holding a large number of beads and capable of dispensing a single bead at a time. An individual bead pack typically will contain a single type of bead which is suitable for use with a variety of different reagents. More than one pack of a given type can be resident on the instrument simultaneously. This allows for selection among the different types of stored beads. The beads involve a biomaterial used to quantitate analytes in solution that is bound to or painted upon an inert support body, such as a glass or plastic bead of about 5 to 7 mm in diameter. The biomaterial generally is selected from an antigen or an antibody. One bead is consumed for each test conducted, and a particular type of bead may be used for any number of different assay types. Vertically oriented bar codes can be provided on the outer periphery of all bead packs which will be accessible for reading by a dedicated CCD bar code reader 212 for the bead carousel 203. The entire bead carousel is housed within a dehumidified chamber maintained at about 10% relative humidity. Again, beads may be dispensed one at a time from any pack. Thus, the beads are originally separate from the reaction tubes, not pre-assembled; and the beads thus are selectively added to the tubes on aboard the instrument 10 depending upon which test is ordered for a sample. After a single type of bead is fed to the reaction tube, the chain 202 advances the reaction tube to a position where it is shuttled to the reaction tube pipetting station 204 where reagent and (diluted) sample can be introduced via the reagent pipettor 205 and sample pipettor 206, respectively, to be combined with the dispensed bead at the bottom of the reaction tube 840. Specifically, the reaction tube is pushed into a reaction tube processing side chain 213b of a reaction tube processor 213 via a reciprocal plunger to position the reaction tube at reaction tube pipetting station 204.

A rotatable sample carousel 207 accommodates a plurality of easily removable tube racks 208, each capable of holding a plurality of sample or diluent test tubes 208a. Deionized water or a protein diluent can be used as the sample diluent. Vertically oriented bar codes can be provided on the outer sidewalls of all tubes which are accessible for reading by bar code reader 210 as the carousel 207 rotates. The bar codes on the sample tubes 208a are manually rotated by an operator to be exposed to and read by the bar code reader 10 before operation of the instrument 210 in the automated mode to inventory the samples and locations thereof on the sample carousel 207. The bar code reader is a scanning laser bar code reader which can read specimen and diluent bar codes on the sample carousel 207 and reagent bar codes on the reagent carousel 209.

The individual arcuate sample racks 208 are loaded upon the sample carousel platform 207a to effectively position the sample tubes 208a such that their bar codes present an unobstructed optical line to the bar code reader 210. The sample tube holders 208b, e.g., hollow sleeves having resiliently-biased tube gripping means, also have a slit in the sleeve wall to expose the bar code on the sample tube. The sample carousel 207 includes a gap 207b through which the bar code reader 210 can scan the reagent carousel 209 located within the sample carousel 207.

The sample (and its diluent) pipettor 206 has a downward projecting pipette tip (not shown) positioned at the end of a pipette arm which can be actuated to travel both vertically (i.e., perpendicular to the plane of the paper) and circularly in arcuate swaths (i.e., along the plane of the paper). The amount of Z-axis translation of pipettor 206 is closely controlled by a level sensing scheme (not shown) so that the pipettor can be assured of dipping enough into the sample or diluent to siphon up the correct amount of fluid, but shallow enough not to damage the operations of the of the pipettor 206 or corrupt the pipettor 206 with fluid which may be carried over to the next tube. This pipettor 206 has an arc of motion which permits it to intersect and travel to and from: (i) the sample tubes and diluent tubes when located at the sample pipetting station 206b on the sample carousel 207, (ii) the sample dilution well 211, (iii) the reaction tube pipetting station 204 where reagent and (diluted) sample are introduced via the reagent pipettor 205 and sample pipettor 206, respectively, and (iv) its probe wash station 206a where water can be pumped through the inside of the sample pipette 206 to flush out the pipette interior and water also is rinsed over the exterior surfaces of the pipette tip after execution of any or each of operations (i), (ii) and/or (iii).

Sample tube elevation sensors 206c preferably can be provided as indicated in FIG. 2A and they can be photoelectric sensors used to detect the height of the sample tube at the sample pipetting station 206b. Also at the sample pipetting station 206b, clot detection optionally can be performed on the sample by the sample pipette 206 using a pressure transducer and an analog-to-digital signal conversion scheme such as those generally known in the field. If the sample fails the clot detection test, the sample can be defaulted and its test discontinued by the computer control.

The sample dilution well 211 is a device, in which a mixing tube is set in rotation, which rapidly mixes quantities of sample, diluent and water to form a homogenous mixture. These materials are added to the well by the sample pipettor 206, and mixing is accomplished by agitation of this well. In turn, disposal of excess mixture from the dilution well is accomplished by rotating the well at high speeds.

The reagent carousel 209 is a rotatable carousel which accommodates a plurality of wedge-shaped reagent packs 209a, 209b, 209c, and so forth, each capable of holding a plurality of different reagents in separate compartments formed in each pack. The immunological reagents are in liquid form and consist of compounds which recognize specific analytes coupled to one of the labels bound to the beads. Three compartment wedges are shown in FIG. 2A. These packs have self-sealing covers, as well as vertical bar codes on the outer periphery of the reagent packs which are accessible for scanning by the sample and diluent bar code reader 210 through sample carousel gap 207b. The entire reagent carousel 209 is housed within a stationary refrigerated chamber (not shown) maintained at about 4° C. The chamber will include an sidewall opening, such as filled with a window, on the outer peripheral side of the reagent carousel 209 which permits the bar code reader 210 to read the bar codes presented on the outer peripheral sides of the reagent wedges as the bar code beam passes through the gap 207b in the sample carousel 207 (held stationary during inventory on the reagent carousel) and the window on the reagent carousel 209. The reagent chamber housing also will have a cover having holes provided which can be aligned with openings in underlying reagent wedge compartments to permit access by the reagent pipettor 205 through the reagent chamber cover.

The reagent carousel 209 and sample carousel 207 each has its own rotary drive so that either can be individually rotated, for example, while the other is held stationary to allow inventory to be taken of either carousel, or to sequentially advance sample tubes around the sample carousel 207 to sample pipetting station 206b during automated assay mode, or to advance reagent wedges around the reagent carousel 209.

A reagent pipettor 205 also has a downward projecting pipette tip (not shown) positioned at the end of a pipette arm which can be actuated to travel both vertically (perpendicular to the plane of the paper) and circularly in arcuate swaths (along the plane of the paper). This probe 205 has access to the reagent carousel 209, a reagent probe wash station 205a and reaction tube pipetting station 204 where the reagent is combined with the bead and sample in a reaction tube 840.

The software of the computer 12 controls the sample pipettor 206 and reagent pipettor 205 to co-ordinate sequential deposits of fluids into the reaction tube at the reaction tube pipetting station 204. That is, if one pipette is detected as being situated over the reaction tube being fed at the reaction tube pipetting station 204, the other pipette will wait for the other pipette to clear the reaction tube before swiveling over the mouth of the reaction tube to deposit its contribution to the reaction tube.

After introducing the appropriate combination of sample and reagent into the reaction tube 840 at reagent pipetting station 204, the reaction tube 840 is indexed once, i.e., moved 90 degrees, where it is picked up and advanced by reaction tube processing main chain 213a of the tube processor 213. The reaction tube processor 213 comprises a serpentine channel 213' having a depth which permits flanges 846 of reaction tubes 840 (e.g., see FIG. 8B) to rest on the top of the channel, and main chain 213a is a top track chain overlying and following the serpentine channel 213'. Main chain 213a has baffles (projections) (not shown) extending downward to contact and incrementally advance the reaction tubes through the serpentine channel 213'. In this way, the tube processor 213 transports reaction tubes along a serpentine path for incubation of the tube contents and ultimately transfers the tubes back to a side track chain 213b also located within the housing for tube processor 213, which, in turn, conveys the reaction tubes to the wash station 214 or returns reaction tubes to the beginning of the serpentine channel 213' for supplemental incubation.

The residence time for the reaction tubes in the tube processor 213 for a single pass is about 30 minutes and tube processor 213 is heated to 37° C. The side track chain 213b in the tube processor 213 is a track chain with arcuate arms that support the reaction tubes at flanges integrally formed at the top of the reaction tubes, similar to chain 202.

In one preferred arrangement, a plurality of reciprocating bars are used as reaction tube shaker bars (not shown), which are located on the bottom of the tube pathways in the tube processor 213 and they are oriented at a direction parallel to the direction of travel of the reaction tubes in the tube processor 213. These shaker bars can bump the bottom portions of the reaction tubes and thereby continuously agitate the reaction tube contents to promote the immunological reactions.

Figure 2B:
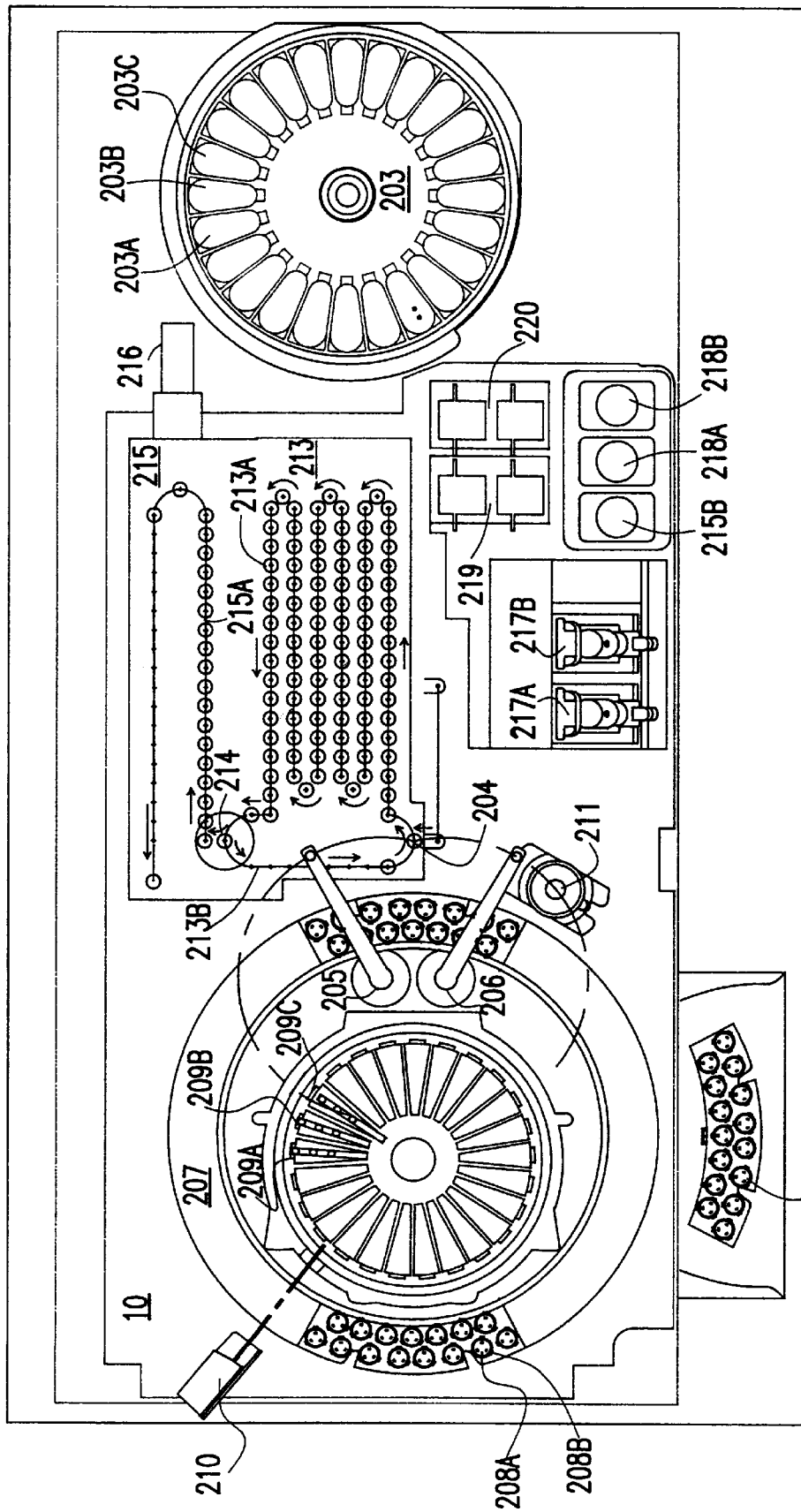
FIG. 2B is a partial schematic view diagram of the flow path of samples and assays through the automated immunoassay analyzer.

After leaving the serpentine channel 213', side chain 213b picks up the reaction tube at the end of the serpentine channel 213', and the main chain 213a circles back to its starting point 90° from reaction tube pipetting station 204, as shown more clearly in FIG. 2B having chain movement direction arrows provided. If additional incubation is desired for a sample, chain 213b is used to circle the reaction tube back to the beginning of the serpentine channel 213'. On the other hand, if the reaction tube needs to be advanced to wash and photometric analysis, the reaction tubes are shuttled out of the tube processor 213 and are picked up by a circular chain and moved to a high speed spin wash station 214. The wash station includes an angled, splined chuck surrounded by a receptacle and a tube elevating device (as shown in FIGS. 8A and 8E). Reaction tubes are first elevated onto this chuck and then rotated about their longitudinal (vertical) axes at high speed, whereby tube fluids climb up outwardly tapered inside walls of the reaction tubes under centrifugal forces to expel fluids along the grooved chuck but retaining the immunoreactive bead within. The waste fluids drain into the liquid waste receptacle. Washing is accomplished by the addition of water into the tube one or more times to the tube during, or followed by, high speed centrifugation.

After washing the beads at the wash station 214 and expelling fluid contents of the reaction tube, the reaction tubes are either: (i) shuttled out of the wash station onto a luminometer chain 215a of a detection station 215 where a substrate is added and quantification made of the analyte of interest, or (ii) returned to reaction pipetting station 204 by side chain 213b where more reagent(s) is added, if necessary for the assay, before the steps of incubation and wash are repeated. The luminometer chain 215a transports the reaction tubes from the wash station 214 to a photo-multiplier tube (PMT) 216a at a reaction tube reading station 216 of detection station 215 for photometric reading, and then the chain 215a moves the assayed tube and its contents to waste. In the detection station 215, the luninometer chain 215a is a side link chain including lower reciprocating shaker bars, similar to those used in the tube processor 213, and the detection station 215 includes an incubator and luminometer block heaters for heating the tube contents after addition of substrate.

In the preferred embodiment, chemiluminescent techniques are used to quantify the analyte. Signal generating chemistries for chemiluminescent techniques include one of either of two formats, each of which cause emission of light from the surface of the processed analytical elements (beads) to produce varying light intensities in response to the concentration of a sample analyte to be quantified. These two different chemistries require the following signal generating reagents stored aboard the instrument 10: chemiluminescent enzyme substrate stored in reservoir 215b for the first chemistry, and first and second trigger reagents stored in reservoirs 218a and 218b for the second type of chemistry. Thus, depending on the chemistry employed by a particular bead, appropriate signal reagents will be added to its reaction tube. For instance, the three signal reagents can be used with each being pumped by a separate, independently controlled solenoid pump at pumping station 220. Each pump is connected to one of three spigots (not shown) which reside over various sites on the luminometer chain 215a.

In the first chemiluminescent technique, alkaline phosphatase substrate is used. Where the bead employs the alkaline phosphatase label, it will receive chemiluminescent substrate in the first luminometer chain position proximal to the tube wash station 214.

The second type of test involves use of acridinium ester with injection of trigger reagents into the reaction tube at the reading station 216 and making an unattenuated count.

Of these two chemistries, it is preferred to label the assay specific antigen or antibody in the reagent with alkaline phosphatase which will cleave a phosphate ester stabilized dioxetane. Decomposition of the dioxetane results in the emission of light photons which can be quantified at detection station 215 and are proportional to the quantity of analyte present. The light signal emitted from the bound labeled analyte on the inert support bead in the reaction tube is measured and the quantity or analyte determined by the computer 12 by reference to an appropriate standard curve. However, it should be understood that other detection schemes such as fluorescence or radioactive ion emission could be used and appropriate labeling of reagent is required.

The reaction tube, as containing the washed bead and substrate solution (e.g., chemiluminescent alkaline phosphatase substrate), is incubated on the luminometer chain 215a for about 5 minutes at 37° C. and advanced to a position in front of the photomultiplier tube 216a where photon counts are measured.

The PMT 216a is part of the reaction tube reading station 216 which also includes a luminometer shutter and attenuator wheel of the types as disclosed in U.S. Pat. No. 5,316,726, which description is incorporated herein by reference. Again, the reaction tube reading station 215 employs the PMT 216a to take light emission measurements on reaction tubes as they pass. A shutter (not shown) is employed to prevent crosstalk between adjacent tubes at the PMT station. This shutter device physically isolates the tube at the PMT 216a from those surrounding it. A rotatable filter (attenuator) wheel (not shown) is mounted between the PMT 216a and the reaction tube position in reaction tube reading station 216 when being read for photon counts. This wheel has three positions: dark (PMT 216a receives no light), unattenuated (PMT 216a receives full light output of the reaction tube); and attenuated (a neutral density filter that is positioned between the PMT 216a and reaction tube to make attenuated counts). The features of such shutters and filter wheels are fully explained in U.S. Pat. No. 5,316,726. For example, a filter wheel can have three sections; an open section for making unattenuated counts; one or more neutral density filter sections for making attenuated counts; and an opaque section for making dark count measurements to calibrate "noise" in the PMT 216a. Photometric data can be gathered by measuring the PMT dark counts and taking an attenuated count (known as the precount), and determining whether the precount value is above or below a preset cutoff value to determine whether an unattenuated measurement may be needed if the precount is below a cutoff value.

The average photon counts per second are converted to analyte concentration by the computer 12 using standard curves which mathematically relate photon counts to concentration. The photon count and concentration information for each reaction tube is archived to a magnetic storage device for later analysis. The concentration for the reaction tube is also sent to display 16 of the computer 12. Periodic calibration with known calibrating solutions maintains the mathematical relationship for a particular instrument 10 and lot of reagents. Calibration of the standard curves may be performed according to protocol such as described in U.S. Pat. No. 5,316,726, which description is incorporated herein by reference.

Fluidic systems are provided throughout the instrument 10 as system of pumps, valves, tubing and reservoirs adequate to provide for the transfer and disposal of fluids, as needed, throughout the instrument. Among these, the pumps include several positive displacement pumps 217a, 217b used in conjunction with the reagent and sample pipettes to permit withdrawing and feeding of precise amounts of sample and reagent. The substrate reservoir 215b stores the chemiluminescent substrate which is pumped via injector pump 219 to the first chain position on luminometer chain 215a at detection station 215 via tubing lines (not shown). Liquid waste drained from the dilution well 211, wash station 214 are collected on-board the instrument 10 in a liquid waste reservoir stored aboard the instrument 10 for appropriate disposal, and the reaction tube and its contents including the bead and any liquid are collected from detection station 215 after completion of the photon count in a solid waste reservoir aboard the instrument 10 for appropriate disposal. Other supporting fluid management equipment such as tubing lines, and so forth, is not shown for sake of simplifying the illustration.

The computer control 12 allows the operator to pick the tests desired for each sample, and, if desired, to prioritize the sample if stat or unstable. A technician informs the computer 12 via keyboard input or other input means of the relevant patient information and tests desired for each sample before placement of the sample's tube on the sample carousel 207, and the location of the sample tube can then be tracked on the sample carousel 207 by the sample tube's bar code. Similarly, the contents of each reagent wedge and bead pack are loaded into the computer's memory and their locations then can be tracked about their respective carousels by their bar codes. The computer 12 can then instruct the instrument 10 to pick the right bead and right reagent and put them in a reaction tube with a particular sample for assay. A system of logic circuitry, cabling, user input/output devices and software is provided for computer 12 which accepts user commands and displays the results of those commands. Devices directly accessible to the user for managing the computer 12 can include a high resolution color monitor, keyboard, trackball, floppy disk drive, CD-ROM drive and speaker. A VDT can be included for computer 12 that tracks the location and status of each sample (e.g., untested/test underway/ tested) intermittently, e.g., about every 18 seconds.

In preparing the instrument 10 for use, an operator first loads all required bulk materials into appropriate on-board storage areas including the reaction tubes, bead packs, reagent packs, bulk fluids including water, probe wash and bead wash solutions, and signal reagents including substrate and trigger reagents. Liquid and solid waste containers should be checked to see if they need emptying. A work list is created either manually of through LIS download. The sample, diluent, and any control or adjustor containing test tubes are loaded onto the sample racks that are placed on the tube carousel, and all tubes are manually rotated so that their bar codes face outwards. Samples which require a known dilution are identified in advance, any samples requiring STAT priority handling are identified.

Inventory is automatically conducted on the test tubes in the sample rack, the reagent packs on the reagent carousel, and on the bead packs on the bead pack carousel, by rotating each respective carousel by its respective bar code reader to interrogate the contents aboard each of the sample, reagent and bead back carousels, and the information from the bar code reader is sent to the computer 12 which tracks the position of all sample tubes 208a, reagent pack 209a, 209b, 209c, and so forth, and bead packs 203a, 203b, 203c, and so forth, within the instrument 10. Not all spaces on each carousel need by filled since the bar code readers will simply identify an empty space on any of the sample carousel, reagent carousel, or bead pack carousel, to the computer 12, and the computer will track the empty space. Position information can be derived and tracked with use of a shaft encoder (not shown) provided on the motor drive to counts steps of the motor such that the position of each sample tube, reagent pack, and bead pack is known by the instrument 10. In conjunction therewith, an internal optical sensor (not shown) formed of an emitter and detector pairing can be built into each carousel to reacquire and recognize, each time the instrument is started up, a fixed metallic reference point or "flag" in the device provided as a home or reference point from which motor steps can be counted from which to get to any position. In this way, the steps of the motor needed to move a sample tube to the sample pipetting station, or a reagent or diluent to the reagent pipetting station, or a bead pack to the bead dispensing position, can be managed by the instrument 10. Samples, reagents or bead packs can be replaced as needed during instrument operation.

After any interruption of the operation of the instrument, inventory is automatically taken again of the various sample rack, reagent pack, and bead pack carousels before testing is resumed. For example, whenever a pause command is hit by the operator at the computer control, or a seal is disrupted in the system, e.g., by opening the housing on the reagent carousel or bead carousel, the instrument 10, when put back on-line, first re-inventories each of the bead carousel, reagent carousel, and sample carousel with the bar code readers to learn any changes possibly made. In this way, the location of each sample tube, or absence thereof (an empty space on the sample carousel 207a), is known by the system, and the reagent and bead packs present on the system are also known. This allows the computer to know what and where things are on the instrument. The sample tubes are then assayed methodically in sequence around the carousel unless prioritization, e.g., for STAT or unstable samples, has been requested at the computer control by the operator.

Figure 3:
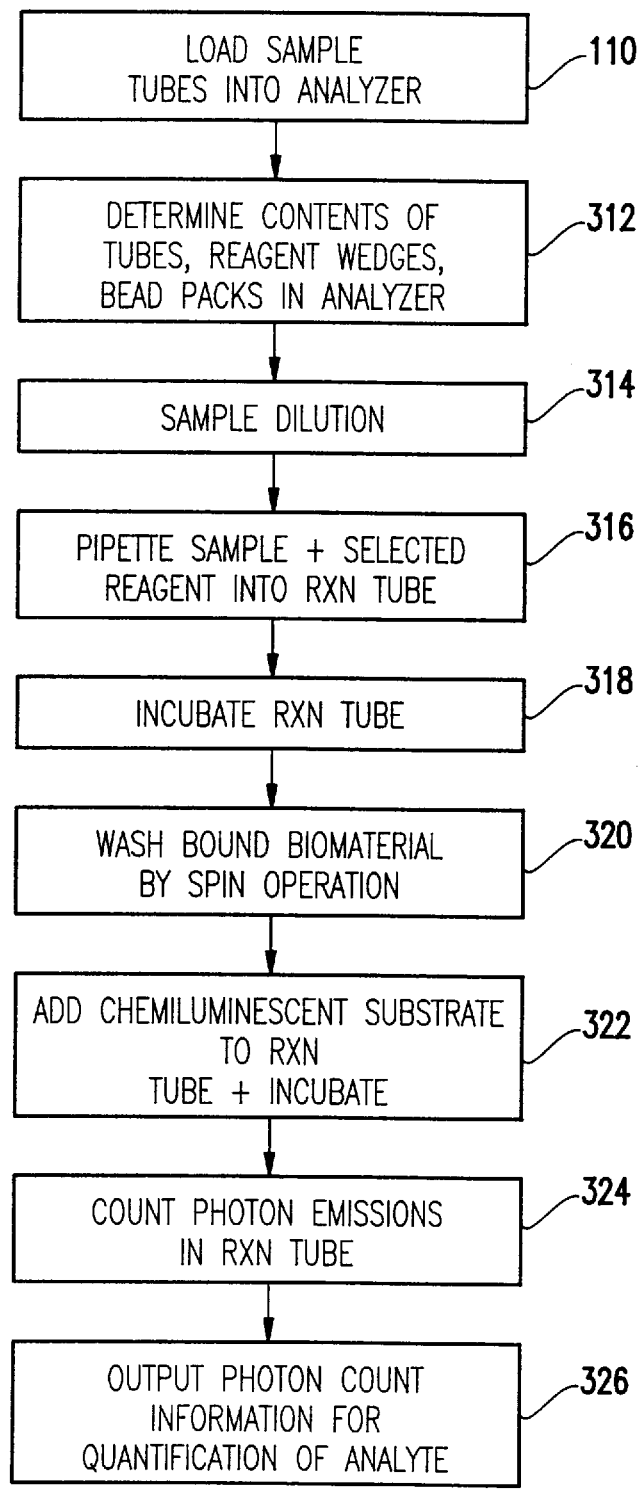
FIG. 3 is a flow chart of the processing steps performed on the assay tubes in the automated immunoassay analyzer.

FIG. 3 illustrates the basic process steps performed by the instrument 10 of the automated immunoassay analyzer. First, at step 310, the sample (and any diluent tubes) are loaded into sample tube holder racks which are positioned on the sample carousel. Second, at step 312, the contents and carousel location of each the sample tubes, reagent packs, and bead packs are determined by bar code readers. At step 314, a portion of sample is withdrawn from a sample tube and mixed with diluent in the dilution well to form a homogenous mixture. The dilute sample is then combined with reagent and a bead at the reaction tube pipetting station in step 316. At step 318, the reaction tubes in which sample and reagent have been combined with a bead are incubated. The time of incubation is determined by the dimensions of the incubation processor and time for incremental advancements in the analyzer. At step 320, the reaction tubes which have been incubated for the requisite period of time are transferred to a high speed washing station. Washing is achieved by rotating the reaction tubes about their longitudinal axes and by pipetting each water into the reaction tubes. High speed rotation of the tubes causes wash fluid to be rapidly removed from the inert support carrying the bound biomaterial which has the bound reagent label. After completing washing in step 320, the reaction tube and inert bead support are free of unbound labeled reagent so that only bound labeled reagent will be detected. At step 322, a chemiluminescent substrate (e.g., phosphate ester dioxetane) is added to the assay tube, and the reaction tube is again incubated for a short time. During incubation, alkaline phosphatase from the reagent which is bound to the inert support cleaves the phosphate ester of the chemiluminescent substrate. Decomposition of the dioxetane releases photon energy; the emitted light photons are proportional to the quantity of analyte present. After decomposition of the dioxetane, the photon emissions are counted at step 324 by a photomultiplier tube (PMT). At step 326, photon count information is sent to the computer for quantitative determination of the analyte.

While a sandwich type assay has been exemplified herein, the instrument 10 is amenable to different immunological chemistries for processing by the system, including any of the formats of sandwich assays, competition assays, or liquid phase capture assays. The system will support many different test categories, such as thyroid function, sex hormones, growth hormones, tumor markers, infectious diseases, allergy testing, immunoglobulin and related proteins and peptides, steroids and other small molecules, therapeutic drugs, drugs of abuse, and vitamins. The system will analyze samples of serum, plasma, or urine, and specific chemistry kits may also handle clarified cerebrospinal fluid or saliva.

The manner of handling certain conceivable errors in the practice of the assay on the inventive instrument is as follows. If there is a lack of required information, such as unreadable bar codes or the absence of information about which tests to run or how to run them, the analyzer can be programmed to verify the availability of all required information whenever the specimen carousel is accessed. If any information is found lacking, the operator can be alerted immediately by audible alarm or via on-screen display. As such, operators can expect the analyzer to process all on-board specimens before requiring further attention. Also, sample-specific fluidics problems could be encountered. These errors could involve insufficient sample or the presence of a clot in the sample. Operators can be alerted immediately of such problems via both on-screen and audible alarms. However, the analyzer will continue to process other specimens while awaiting operator intervention. If there are hardware problems, such as fluidic component failures, clogged inlet filters, and so forth, operators can be alerted immediately of such via both on-screen and audible alarms. Until an operator intervenes, sampling operations should be suspended, but tube processor operations can continue.

More detailed descriptions of the sample tube holding system, bead pack, reagent pack, wash station and dilution well subsystems of instrument 10 are provided hereinafter to further illuminate the specific manner of operation of the instrument's components.

Figure 4A:
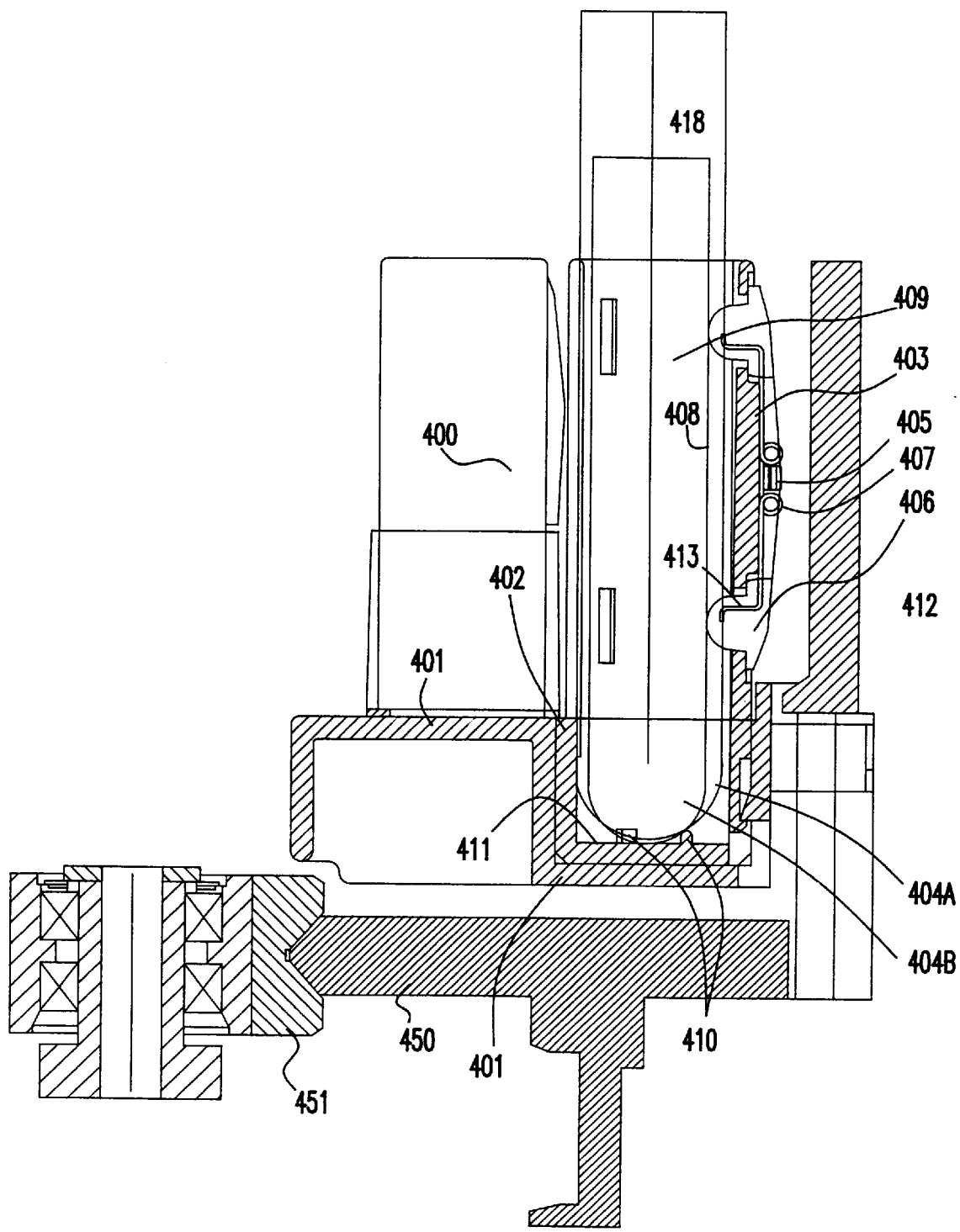
FIG. 4A is a cross-sectional side view of a rack with a sample container holder of the invention mounted on a carousel.

An improved sample container rack is provided in the inventive instrument. Referring to FIG. 4A, there is a sample container rack 400 including a base or support platform 401 and an upright cylindrical sample container holder sleeve 402 integral with the base 401. The rack can include a plurality of such sample container holder sleeves, but only one representative sleeve is depicted in FIG. 4A for illustrative purposes. The rack and its holder sleeves can be formed by injection molding of plastic. Sample container holder sleeve 402 is a cylindrical-shaped shell having a mouth or opening 418 at its upper end and also has a vertically extending slot (not shown) provided in the sidewall 403 of the sleeve, whereby a sample container 404a or 404b (superimposed in FIG. 4A for illustrative purposes only) can be manually rotated within the sleeve 403 until an identifying means (not shown), such as a bar code, is visible and readable through the slot. The sample container holder sleeve 402 also includes a plurality of sample container gripping means 405 (with only one representative gripper means depicted in FIG. 4A to facilitate the illustration), preferably spaced equidistantly around a circumference of the sleeve (other than at the slot region). Each gripping means 405 has at least one projection tab 406 that is resiliently urged inward through an aperture 412 provide in the holder sleeve sidewall 403 by virtue a spring-like means 407 mounted on the exterior of sleeve sidewall 403 to cause the projection tab 406 to be urged against a sidewall portion 408 of the sample container 404a or 404b to center the sample container 404a or 404b within the sleeve well 409 and maintain the sample container 404a or 404b in an upright orientation. The projection tab 406 can be formed of a rigid, semirigid, or elastomeric material, and preferably is a semirigid elastomeric material, such as rubber, having a spring arm 413 embedded therein. Preferably three or more gripping means 405 are located equidistantly around a circumference of the holder sleeve 402. In one preferred mode of the invention, three gripping means 405 are equidistantly spaced around a circumference of the sleeve 402, where each gripping means 405 has a pair of projection tabs 406 that are aligned vertically and the projections are urged simultaneously against a side wall of the sample container. As the sample container is grabbed simultaneously and symmetrically from all sides during its insertion into the sleeve well 409 by the plurality of such gripping means 405, centering of the sample container will be assured. Also, abutment posts 410 can be arranged on the base 411 of the holder sleeve 402 to further facilitate centering of the sample containers 404a or 404b about the central longitudinal axis z of the sleeve 402. The sample container rack 401 can be positioned on and supported on a rotatable carousel aboard an immunoassay analyzer, so that the various sample containers, as held in centered manner in the holder sleeves, can be transmitted to a pipetting station on the instrument.

Figure 4C:
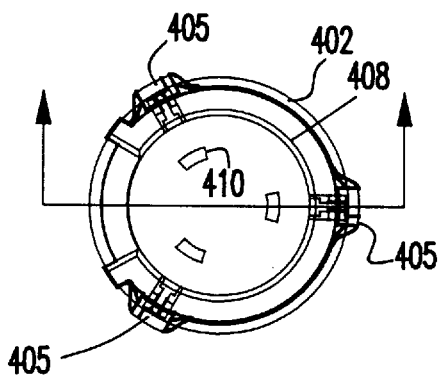
FIG. 4C is a top view of the sample container holder sleeve of FIG. 4B.
Figure 4E:
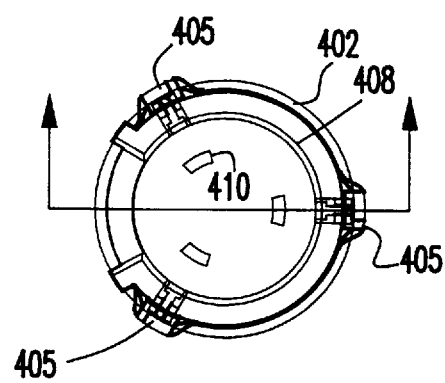
FIG. 4E is a top view of the sample container holder sleeve of FIG. 4D.
Figure 4B:
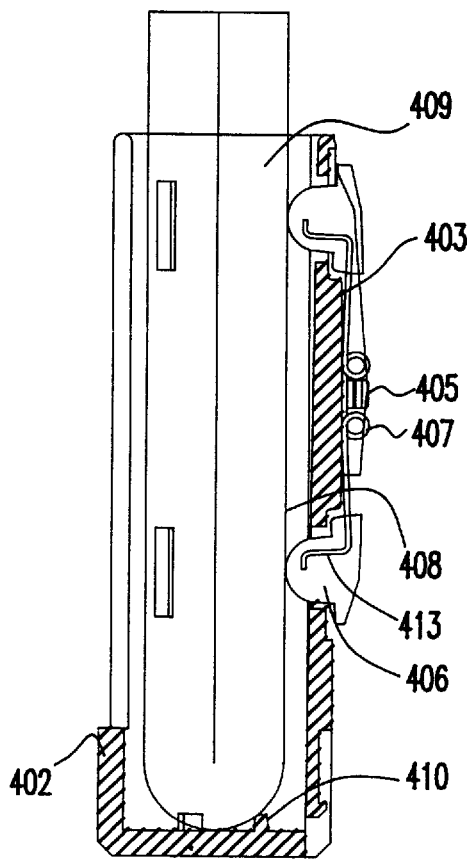
FIG. 4B is a fragmentary cross-sectional side view of an individual sample container holder sleeve of the invention holding a relatively small test tube.

Referring now to FIG. 4B, there is an isolated depiction of individual sample container holder sleeve of the invention holding a relatively small diameter test tube 408. FIG. 4C is a top view of the sleeve holder of FIG. 4B indicating the presence and locations of three gripper means 405 equidistantly spaced around a circumference of the holder sleeve 402 to simultaneously and symmetrically grip the sample container 408 from different sides. The elements labeled in FIG. 4B and FIG. 4C have the same meaning as described herein relative to FIG. 4A.

Figure 4D:
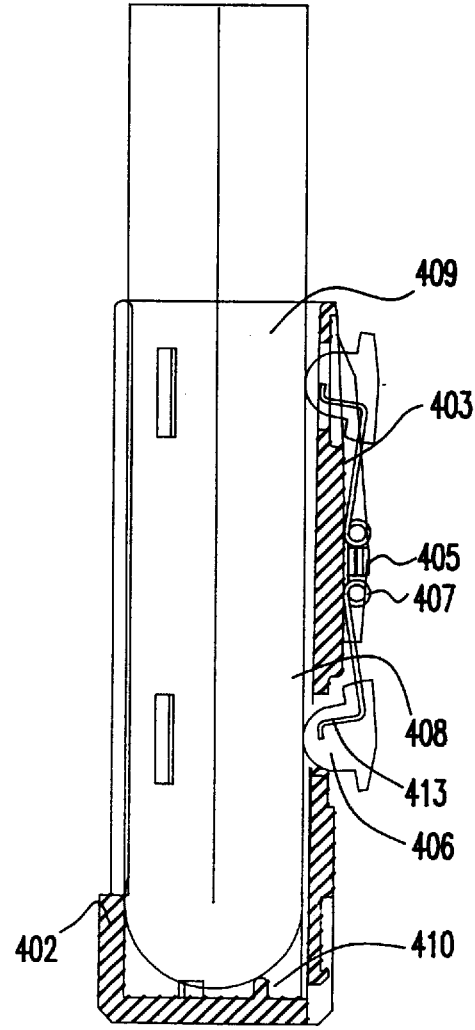
FIG. 4D is a fragmentary cross-sectional side view of an individual sample container holder sleeve of the invention holding a relatively large test tube.

Referring now to FIG. 4D, there is an isolated depiction of individual sample container holder sleeve of the invention holding a relatively large diameter test tube 408. FIG. 4E is a top view of the holder sleeve of FIG. 4D indicating the presence and locations of three gripper means 405 equidistantly spaced around a circumference of the holder sleeve 402 to simultaneously and symmetrically grip the sample container 408 from different sides. The elements labeled in FIG. 4D and FIG. 4E have the same meaning as described herein relative to FIG. 4A.

Figure 4F:
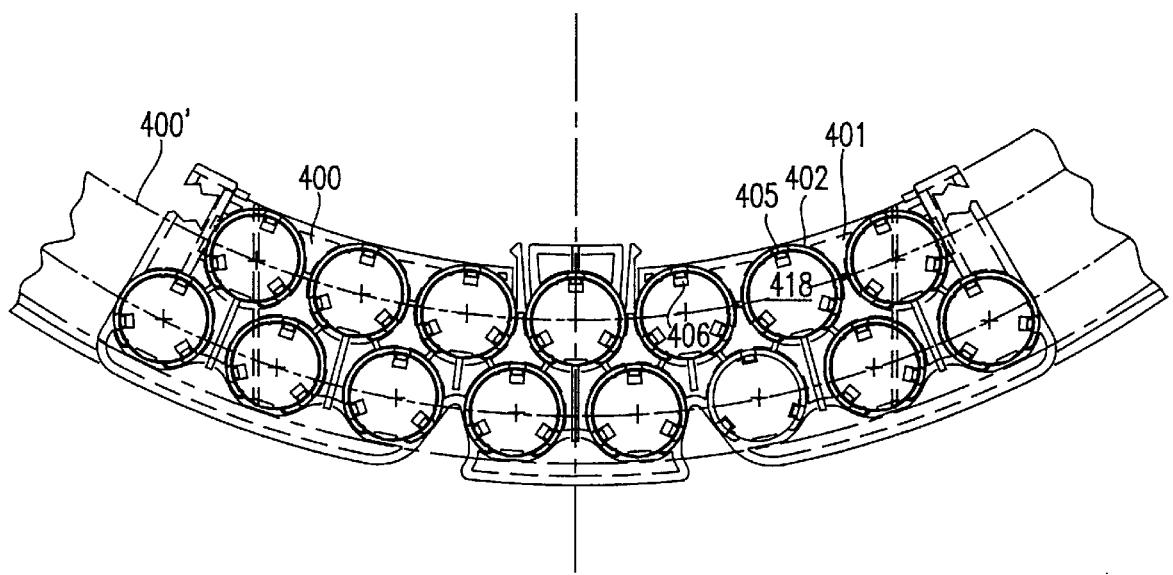
FIG. 4F is a top view of a carousel segment supporting a sample container rack of the invention.

In FIG. 4F, an arcuate tube holding rack 400 is shown in top view that can be supported on a portion of an underlying arcuate carousel platform 400' aboard an immunoassay instrument. The sample carousel 400'. The rack 400 is an integral object that can be moved at the will of the operator to any available desired location on such a carousel, space permitting. The rack 400 is shown as capable of supporting 15 tubes for exemplification purposes. If more than one rack is used, the various racks can have an outer profile that is the same geometry, or can differ from each other, without limitation. The size of the rack and number of holder sleeves provided on each rack is not particular limited other than by the spatial limitations of the carousel 400', as to the rack configuration, and of the rack, in terms of the number and arrangement of holder sleeves it has room to support.

The sample container rack of the invention allows the sample containers, as received, including sample containers received in nonuniform sizes, to be loaded directly into an automated analyzer without the need to devote time and effort to assessing the size of the original sample container or transferring the sample contents into a prescribed size of sample tube. Also, the sample container rack of the invention automatically centers the sample container for pipetting operations regardless of the size of the sample container for a wide range of test tube sizes.

To remove aliquots of sample from a sample container held in a holder of the inventive rack, a downward projecting pipette (not shown) can be positioned at the free end of a translatable pipetting arm. To perform pipetting operations, the pipette tip must be inserted into and out of the sample tubes (and reagent containers) by moving the pipetting arm vertically down and then back up, respectively. The amount of vertical translation of the pipetting arm is closely controlled by a level sensing scheme (not shown) so that the pipetter can be assured of dipping into a sample container (or reagent container on a reagent carousel) far enough to siphon up the correct amount of sample or reagent, but shallow enough not to damage the operations of the pipetting station or corrupt the pipetter with sample or reagent which may be carried over to the next assay tube. A pair of precision syringe pumps can be connected to the pipetting station, where, preferably, one of the syringe pumps is calibrated for large volumes while the other is calibrated for small volumes. A probe wash station can be provided having separate wash wells for simultaneously flushing the inside and outside of the pipette tip. Extensive probe flushing on every pipetting cycle eliminates detectable sample carryover. The probe wash station should also have a fresh water supply. In a preferred embodiment, the pipetter may pick up one or more small air bubbles separated by water to aid in transfer of sample and reagent to an assay tube.

In usage of the sample container rack system of the invention, an operator manually uncaps and loads specimens in the sample containers, as received, or a different sample container, if desired, into the sleeve racks arranged on the carousel. By way of example only, and not limitation, the following types sample containers can be supported by the rack system of the invention: a) primary blood collection tubes such as in the following sizes: 12×75 mm; 12×100 mm; 13×75 mm; 13×100 mm; 16×75 mm; and 16×100 mm; b) test tubes such as in the following sizes: 12×75 mm; 12×100 mm; 13×75 mm; 13×100 mm; 16×75 mm; and 16×100 mm; and c) tube-top sample cups.

The vessels are inserted manually into racks of the invention which can accept a wide range of specimen containers. The vessels are then manually rotated until their bar codes are visible through slots provided in each rack, and the rack is installed onto the sample carousel. Each rack can accept up to 15 specimens or more, and a plurality of racks, such as a total of up to six racks or more, may reside on the sample carousel at any time, depending on the relative sizing of the racks and carousel. As such, a total of up to 90 or even more specimens may be simultaneously resident on the analyzer using the rack system of the present invention. An operator may remove a rack from the analyzer at any time to supplement or replace the supply of specimens. For tracking purposes, each rack position should be designated, for example, as position A, B, and so forth, in both human and instrument readable forms. This information will be readily visible while looking at the sample rack carousel, and, preferably, will also be displayed graphically on a computer display screen. The display screen can also be programmed to include other details about specimen sampling in the software description documents, including, for example, which racks are present on the instrument; the location of these racks in relation to each other; the location on these racks of specimens and diluents; the locations of specimens which have been processed are thus no longer needed; the locations of specimens which cannot be used due to some error condition; and the operating status (whether racks may be accessed by the operator).

The analyzer instrument can be provided with means to identify specimens either automatically via bar code or through operator input. In the former case, specimens will be identified by an accession number or other unique identification imprinted on a label in bar code format. To allow automated identification, the operator will need to first attach this label along a linear axis of the specimen tube and then insert the tube into a rack such that the label is visible. An on-board bar code reader can then be used to automatically associate the specimen with its location in a given rack. If bar codes are not available, the operator may install specimens into racks and then inform the computer controls of the analyzer of the appropriate accession numbers via keyboard and/or pointing device input.

Once specimens have been loaded in the sample container racks, and identified, the sampling process will entail the following steps:
 a) rotation of the sample carousel to position the selected specimen at the sampling position
 b) identification of the specimen tube size
 c) positioning of the sample probe at the specimen surface via level detection
 d) withdrawal of an appropriate aliquot (e.g., about 5 to 100 µL)
 e) detection of probe clogging due to particulates or clots in the specimen
 f) detection of other fluidic problems which might invalidate the current test
 g) transfer of the aliquot to either a reaction tube or a sample dilution well as required
 h) washing of the sample probe in preparation for processing of the next specimen.

Operators may specify the order in which samples are processed. STAT specimens will always be processed first, while remaining samples may be handled in any of the following orders: a) sort by rack and by position within rack (default); b) process user designated priority tests first; c) sort by specimen accession number; or d) sort by test type.

In one mode of usage, the automated analyzer using the sample container rack of the invention is programmed to prompt the operator to select a primary or secondary default tube type. In the former case, the tube length will determine the maximum depth at which the specimen surface should be located. If the fluid surface is not detected at or above this level, sampling of the specimen will be aborted. This will prevent contamination of the probe by either solids or RBC separation gel in the specimen tube. Where secondary is the chosen default tube type, the probe will travel all the way to the tube bottom in search of a fluid surface. Operators will be allowed to designate individual tubes as primary or secondary.

Also, it may be desirable to dilute specimens prior to assay at the request of the operator or automatically. This is accomplished via mixing of a specimen aliquot, water and quantity of a concentrated diluent in the sample dilution well described herein. Diluents, if so desired, can be supplied in screw-cap tubes accepted by the on-board specimen racks.

In another subsystem of the inventive instrument, there is a unique reagent container device utilized that is a multi-compartmented vessel having reagent contents thereof accessible via a self-sealing lid means that functions according to a "living hinge" principle, such that the lid means is biased to provide automatic self-sealing action such that the lid reseals access holes of the multi-compartmented vessel once a reagent extraction device clears the access holes of the vessel compartment openings and openings provided in the lid.

Figure 5B:
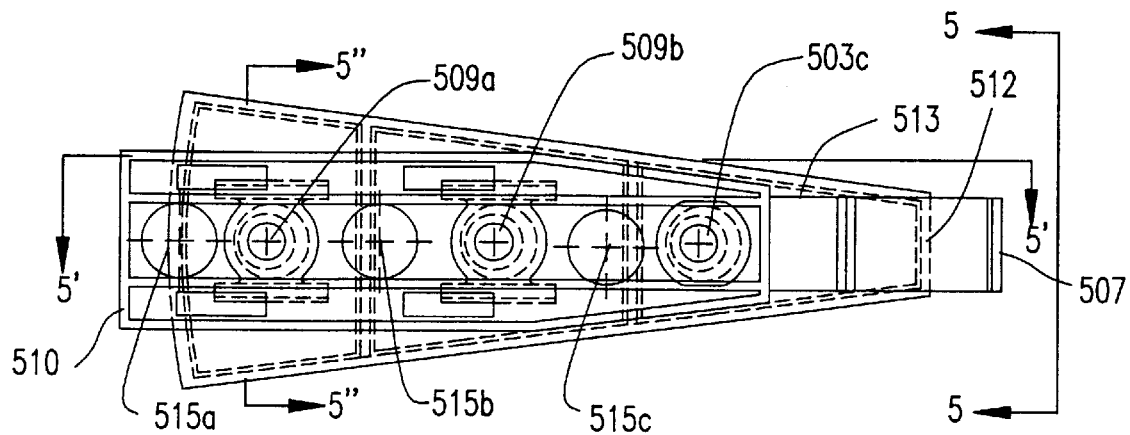
FIG. 5B is a top view of the reagent container with re-sealable lid of FIG. 5A.
Figure 5A:
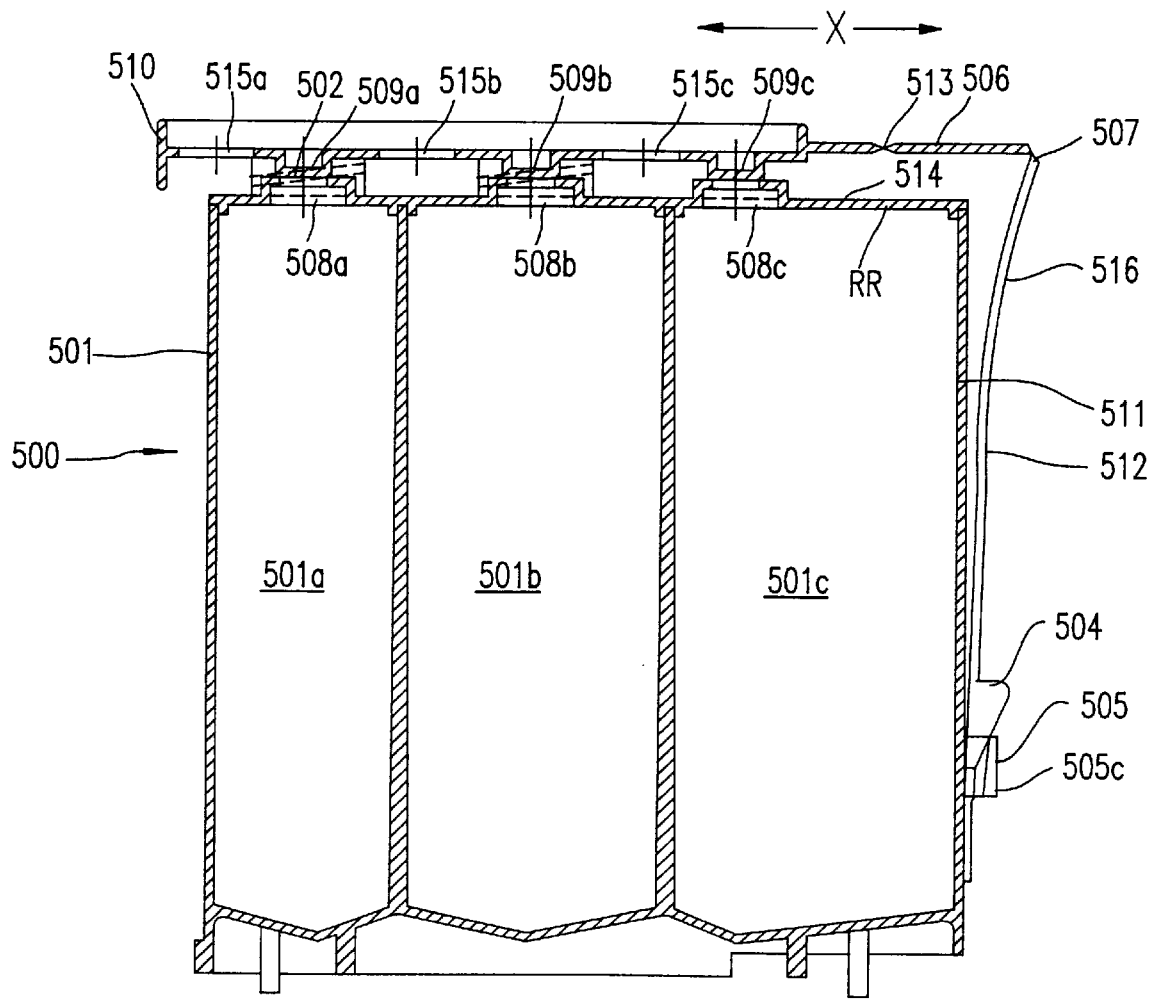
FIG. 5A is a fragmentary cross-sectional side view of a reagent container with re-sealable lid of the invention.

Referring FIG. 5A, there is shown a reagent container 500 of the invention with its self-sealing lid mechanism 503 attached thereto. The container 500 itself has a reagent vessel 501 comprised of a plurality of separate reagent storing compartments or wells, indicated as three compartments in this example of 501*a*, 501*b*, and 501*c*. These compartments share a common cover 514, which provides compartment openings 508*a*, 508*b*, and 508*c*, respectively. The openings 508*a–c* have a size adequate to permit a reagent extracting pipette (not shown) to be introduced into and retracted from the compartment in an unencumbered manner. The reagent container can have any convenient geometric shape. The reagent container 500 preferably is provided in an overall wedge-like shape, as indicated in the top view of FIG. 5A, which allows a plurality of such reagent "wedges" to be situated side-by-side in a pie-like configuration on a carousel, thereby permitting a wide variety of reagents types to be accessible for immunoassay operations. Alternatively, the reagent compartments can be positioned in a linear array to provide a box-shaped reagent container.

The reagent vessel 501 can be prepackaged with its compartments pre-filled with selected reagents deposited in the various compartments. The openings can be optionally pre-sealed with a detachable adhesive-coated metallic foil. The reagent container can be loaded on a reagent carousel; sealing foil removed (if any); and then lid means 503 attached to the exterior of vessel 501, in a manner described in greater detail below.

Figure 5C:
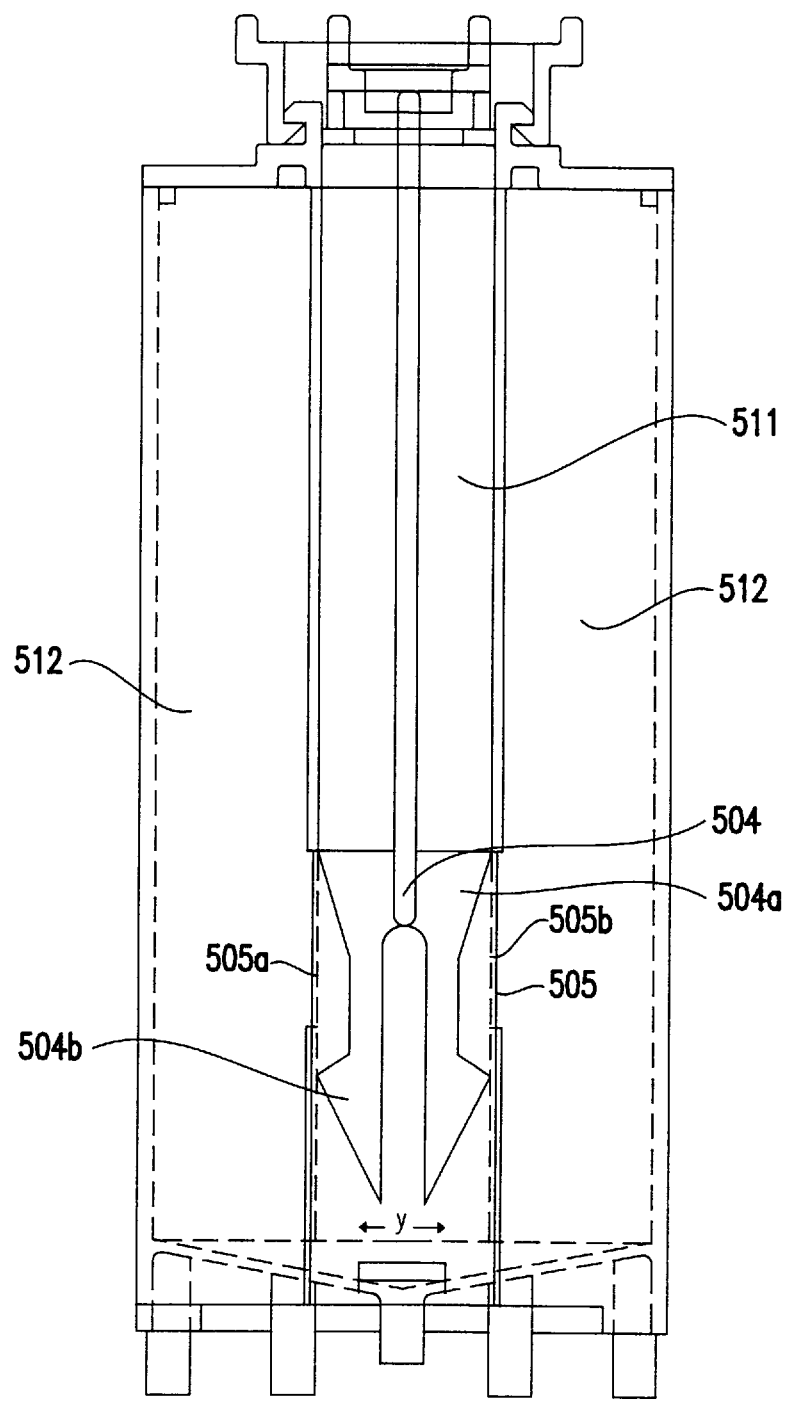
FIG. 5C is a rear view of the reagent container and re-sealable lid along the direction 5—5 indicated in FIG. 5B.

An important aspect of the invention resides in the self-sealing lid means 503 which automatically reseals the reagent container 500 between any intermittent reagent extractions from the container without the need for external force to be applied to effect re-closure. The lid means 503 is a molded plastic member with spring-like biasing force generated by a bend 516 located below the hinge 507 that compels the lid means to release any bias force by movement of the horizontal arm 506 along the x-direction towards projection 510 until caps 509*a–c* cover openings 508*a–c* to move lid means 503 (back) to a "closed" position (see FIG. 5G).

Figure 5D:
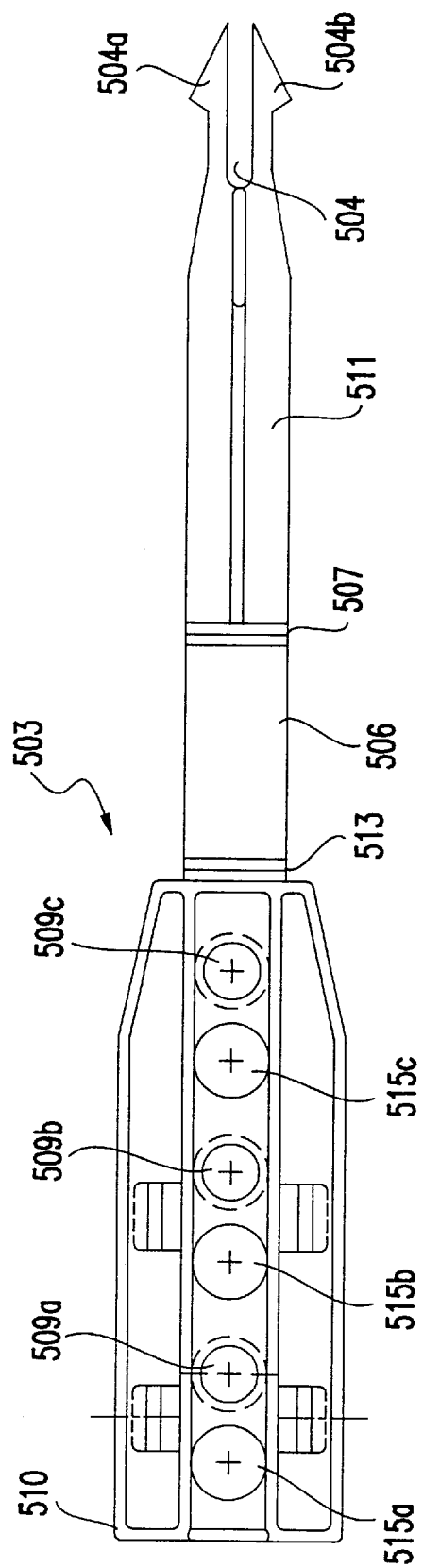
FIG. 5D is a fragmentary top view of the lid means of the invention.

When external force is supplied to projection 510 in the x-direction adequate to overcome the normal bias force acting in the opposite direction, the arm 506 displaces rearward in the direction of hinge 507 until caps 509*a–c* are pushed far enough to horizontally clear the underlying compartment openings 508*a–c*. As can be more easily seen in FIG. 5D, the lid caps 509*a–c* alternate with openings 515*a–c*. Depending on the location of arm 506, either the caps 509*a–c* or openings 515*a–c* can be aligned with the underlying openings 508*a–c* in the cover 514 of the reagent vessels. The caps 509*a–c* are sized slightly larger in diameter than openings 508*a–c*, respectively, such that the caps cover the openings when the lid means is in its normal position, versus its active position (described in greater detail below). As best seen in FIG. 5D, a second hinge 513 is also provided at a location approximately midway between opening 515*a* and hinge 507. Hinges 507 and 513 can be formed as thinned portions in the lid means 503 during molding. The hinges 507 and 513 extend side edge-to-side edge and run perpendicular to the major length direction of lid means 503. The first hinge 507 allows the arm 506 to generally slide forwards and backwards. The second hinge 513 relieves stress created in the arm 506 when it is pushed backwards while traversing and restrained by the ramp guide means 551a, 551b (FIG. 5E) such that the arm 506 can retract along a horizontal line without tending to significantly arc (see FIG. 5H). Both hinges 507 and 513 are formed as thinned plastic regions in the arm molding which form flexure points along the arm 511 and arm 506, respectively. However, the thickness of the hinge must left sufficiently thick to prevent failure of the crimped or thinned hinge-like portion after only limited numbers of flexures.

The lid means 503 also is attached to the side wall 512 of reagent vessel 501 at its lower end. The lid means 503 can be preassembled with the reagent vessel or attached on site when used. For example, when a fresh reagent wedge 500 is provided to a carousel of an immunoassay analyzer, the protective foil can be stripped from the upper surfaces of openings 508a–c to expose openings 508a–c, and the lid means 503 can be attached to the container before or after these steps.

Another aspect of the reagent container sealing system 503 of this invention is that the alternating caps 509a–c and openings 515a–c in the horizontal arm 506 of the lid means 503 are maintained in translational alignment over the underlying openings 508a–c of the reagent vessel compartments by use of guide means (not shown in FIG. 5A for sake of clarity as to other above-discussed features) to restrict sideways movement of the horizontal arm 506 during its movement over the upper surface of cover 514.

Figure 5E:
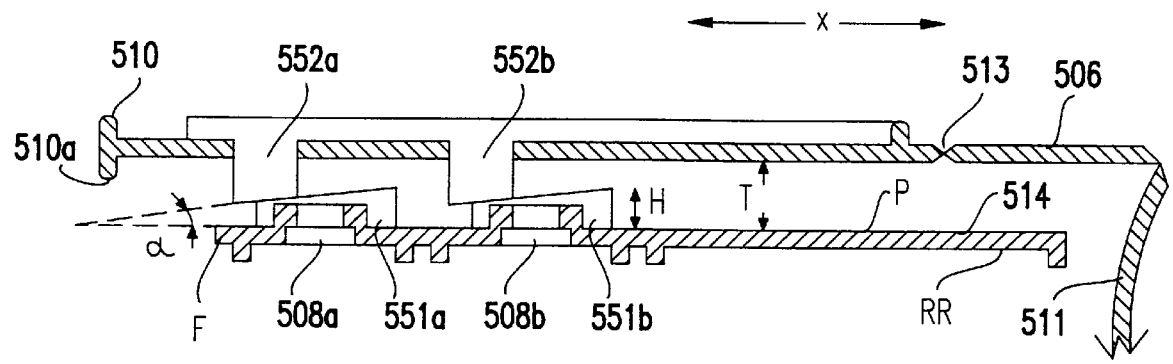
FIG. 5E is a fragmentary side view along direction 5'—5' of FIG. 5B of the of the self-sealing horizontal arm of the lid means and ramp guide means system of the present invention.

As seen in FIG. 5E, ramp guide means 551a and 551b are provided on the upper surface of cover 514. Some features of the lid means and reagent vessel, not essential to understanding this aspect of the invention, have been omitted from FIG. 5E to clarify the illustration. The ramps 551a and 551b, and corresponding lid projections 552a and 552b, are inclined at the same relatively small acute angle α relative to the horizontal plane P extending coplanar with the upper flat surface portion of cover 514, such as inclined from the horizontal direction (i.e., the x-direction) at angle ranging from about 5° to 15°, preferably about 10°. The direction of inclination of the ramp guide means 551a, 551b steeps up from the front F of cover 514 towards the rear RR of cover 514.

The acute angle α established for ramps 551a and 551b (and projections 552a and 552b) must be large enough such that as soon as lid means 503 is pushed rightward along the x-direction via force applied at projection 510 (in the perspective of FIG. 5), that the caps 509a–c of lid means 503 are contemporaneously translated upward up the ramps 551a and 551b and out of contact with the surfaces of the cap openings 508a–c of the cover 514. Thus, sliding friction between the cover 514 and lid means 503 is avoided without resorting to a loose interfit of lid 503 and cover 514. On the other hand, the acute angle α of the ramps 551a and 551b must be not be set too large so as to make access difficult to openings 509a–c of cover 514 when lid means 503 is pushed rightward along the x-direction via force applied at projection 510. That is, with an ever steeper angle for ramps 551a and 551b, the horizontal profile of openings 515a–c in the lid 503 is diminished.

Figure 5F:
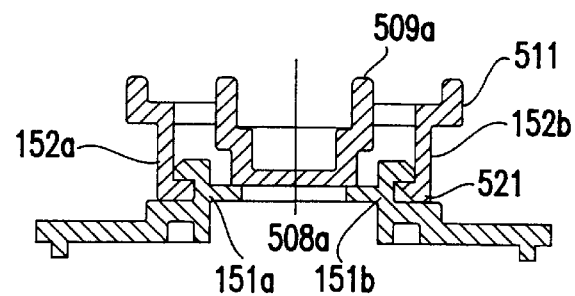
FIG. 5F is a fragmentary end view of along direction 5'—5' of FIG. 5B showing an interlocking ramp guide means and horizontal arm system for the lid means.
Figures 5G, 5H:
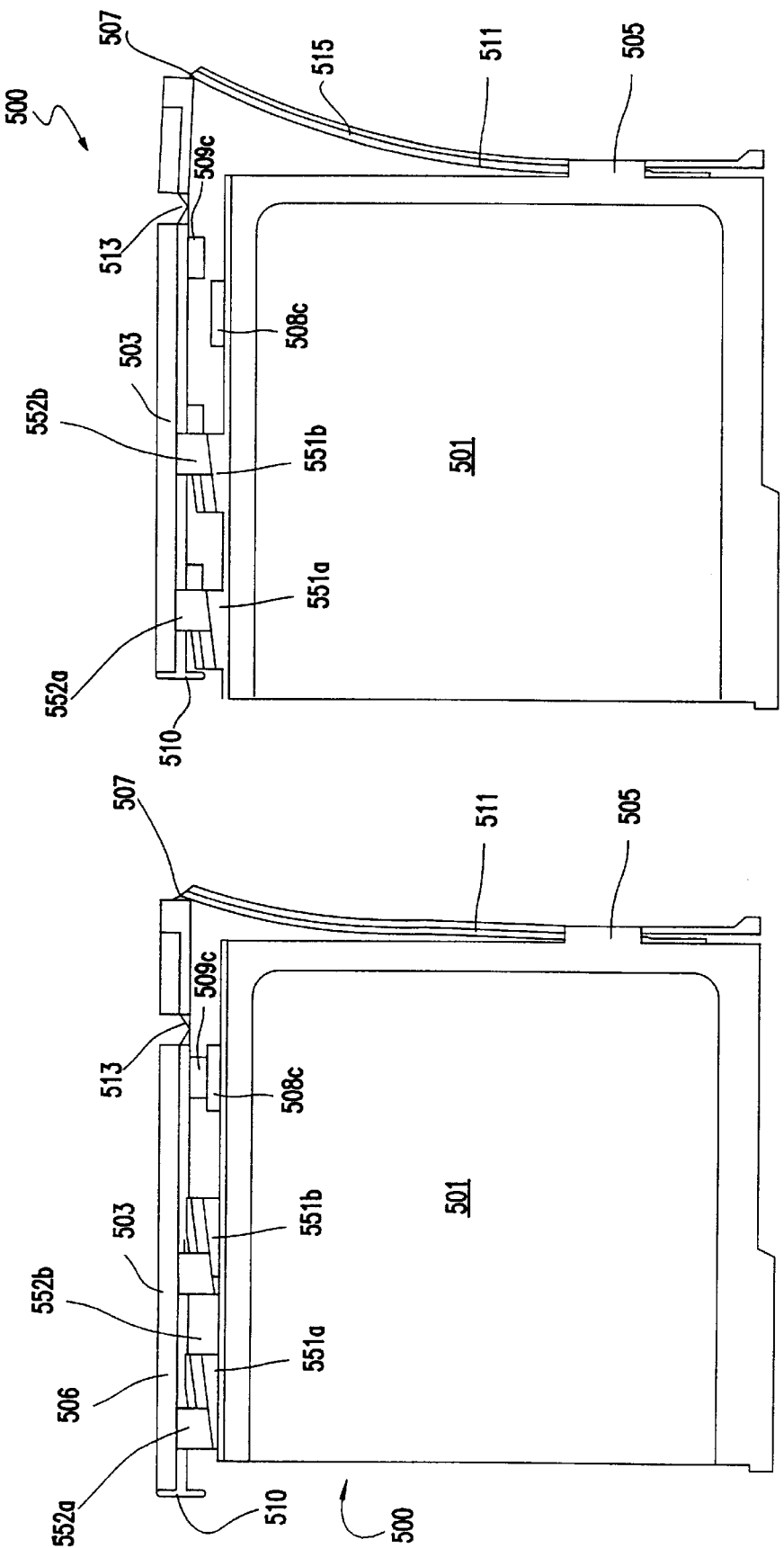
FIG. 5G is a side exterior view of a reagent container with a re-sealable lid of the invention in a closed position.
FIG. 5H is a side exterior view of a reagent container with a re-sealable lid of the invention in an open position.

The ratio of the vertical height H of the ramps 551a, 551b, relative to overall gap T between arm 506 and cover 514,
that is, the ratio H/T, is about 40–50% for the highest point of each ramp and about 5–15% at the lowest end of each ramp. The arm 506, when horizontally displaced over the upper surface of cover 514, is mechanically guided by ramp means 551a, 551b via downward projections 552a, 552b on arm 505 having means to interconnect with the ramp means 551a, 551b while permitting inter-sliding movement along a single line of direction. For example, as shown in FIG. 5F, interlockable hooks can be integrally formed on the ends of projections 552a, 552b and ramps 551a and 551b to allow slidable interfitting of these components. In more detail, projection 552a actually is comprised of a pair of projections 152a and 152b located on opposite sides of the related cap 509a on arm 506. Similarly, ramp guide means 551a, is actually comprised of a pair of upstanding members 151a and 151b extending from cover 514 on either side of cover opening 508a. Projection 152b, like its companion projection 152a, terminates in a downward projecting hook 521 which mechanically interfits with an upstanding hook or rail 511 formed in ramp guide portion 151b.

Therefore, an important aspect of the invention is that when force is applied to projection 510 in the x-direction by an operator or electromechanical actuator, the projections 552a and 552b will slide up ramp guide means 551a and 551b, respectively, avoiding sliding friction without resorting to loose interfit between the lid 503 and cover 514. Preferably, when access to the reagent compartments is desired, projection 510 is horizontally pushed with adequate force to overcome the normal opposing bias force in the lid means 503 caused by spring-arm 511 until caps 509a–c in the arm 506 clear compartment openings 508a–c and openings 515a–c instead align over the compartment openings 508a–c.

The lower end of arm 511 of lid means 503 can be attached to the sidewall 512 of the reagent vessel by any convenient means. As one technique to attach the arm 511 of lid means 503 to the inner vertical sidewall 512 of the reagent container 500, as shown in FIG. 5C, the inner vertical wall 512 of the reagent vessel 501 can have a sleeve 505 comprised of two upstanding walls 505a and 505b, which define an opening sized to receive tongue member 504 of arm 511 of lid 503, and a cover side 505c (see FIG. 1) integral with side walls 505a, 505b which prevents movement of the arm off the sidewall 512. The tongue member 504 has a pair of prongs 504a and 504b that are normally biased outward in the y-direction, but which can be displaced inward in the y-direction by operator handling.

FIG. 5D is a fragmentary view of the lid means 503 alone, where the labeled elements have the descriptions set forth herein. The prongs 504a and 504b of tongue 504 of the lid means, are inserted into the sleeve 505 through opening 513 to grip the respective walls 505a and 505b due to the outward spring-like bias of the prongs 504a and 504b, to attach the lid means 503 to the reagent vessel 501. Ribs or flanges (not shown) also can be formed on the inner sides of walls 505a and 505b of sleeve 505 to mechanically enhance the interlock between the tongue 504 and sleeve 505.

The reagent wedges, i.e., "reagent packs", of the invention will simultaneously support a relatively large number of assay types, e.g., up to 24 or more, each requiring up to 3 or even more liquid reagents, without reduction of the on-board assay capacity of an automated chemical/biochemical analyzer. The reagent packs of the invention also provide the ability to store and preserve reagents on-board an immunoanalyzer, for example, for relatively extended periods of time, e.g. one month, without detectable degradation. The reagent packs of the invention also permit reagents to be positively identified via an attached bar code.

A rotating carousel described herein accommodates a plurality of wedge-shaped reagent packs, each reagent pack capable of holding a plurality of different reagents in different compartments thereof. These packs include instrument actuated covers as well as vertical bar codes which are accessible to the specimen and diluent bar code reader. The entire carousel is housed within a refrigerator chamber maintained at about 4° C.

By way of illustration, in immunoassay analysis, the reagents are supplied in liquid form, and are used to generate a detectable signal proportional or inversely proportional to the concentration of analyte in a specimen. During processing, they are deposited into individual reaction tubes associated with a bead having an appropriate biomaterial coated on its surface for the test needed on the sample. Reagents are contained within disposable packs, each bearing a plurality, e.g., up to three or more, different reagents in separate respective compartments. These packs protect their contents from the environment by virtue of their instrument actuated lids and their construction from colored transparent materials. The packs are also constructed of a material, such as plastic, that is sufficiently translucent to permit operators to visually observe from the outside the fluid levels within.

A plurality, e.g., up to 24 or more, of different reagent packs can be simultaneously resident on the analyzer instrument, and the operator may replace or supplement the supply of packs at any time. A quantity of reagent may be consumed from one or more of the chambers of a reagent pack for each test conducted. A particular reagent pack may be used for several different test types, but reagent/bead lot matching is required for each test type the reagent pack supports. A given test must use reagents from one and only type of reagent pack. More than one pack of a given type may be resident on the analyzer instrument simultaneously. Reagent packs serve the following functions:

a) to protect the reagents they contain from evaporation;
b) to protect the reagents they contain from contamination;
c) to package the reagents in a manner convenient for operator access and handling;
d) to facilitate the dispensing of reagents into each reaction tube as needed;
e) to provide the necessary space for attachment of labeling; and
f) to enable visual estimation of reagent inventory by the operator. Reagent packs can be bar code labeled with all the information needed to identify them to both an analyzer instrument and the operator.

A high performance sample dilution system is also provided in the inventive instrument. In the sample dilution system of this invention, there is a unique combination including a dilution well waste chamber, a dilution well spinning means located in the base of the chamber, and a re-useable dilution well removably nested in the spinning means that is used to mix and dilute liquid samples by rotary motion imparted by the spinning means.

Referring to FIG. 6, there generally is shown a sample dilution system 610 of the present invention. Specimens may be diluted prior to assay either at the request of the user or automatically. This is accomplished via mixing of a specimen aliquot and a quantity of a diluent, such as a protein diluent or deionized water, in the sample dilution system 610. The dilution well waste chamber 611 is an enclosure defined by chamber walls 620 of chamber body 615 and a removable dilution well cover 613. As illustrated, the waste chamber 611 can be conveniently formed at least partly recessed in a work station table top 612, such as of an immunoassay instrument. The removable dilution well cover 613 has a central opening 614 for pipette access. Concentric projections 614' and 614" extending from the lower side 613' of the cover 613 help direct a pipette into the mouth 631 of the dilution well 625 and channel waste fluids during well cleaning, respectively. The chamber body 615 includes flange 617 retaining O-ring 616 which forms a seal with the rim 618 of the cover 613.

The chamber body 615 is stationary and defines inner sidewalls 620, and bottom 621 having a drainage port 636 and a centrally located opening 619. The central opening 619 houses a rotatable dilution well spindle 622. Bearings 624 are provided between the stationary chamber body 615 and the rotatable spindle means 622. The spindle 622 includes a hollow sleeve 622' defining a recess 623 sized to allow the dilution well 625 to be nested and frictionally interfit inside the spindle 622 such that the dilution well 625 will travel in rotation with the spindle 622. The spindle can be driven in rotation by adjustable motor 628 having drive shaft 629 mechanically connected to spindle 622 via a coupling 630. Teflon seals 626 are also preferably provided between the chamber body 615 and spindle 622, as shown, to provide a water-tight system that seals the bearings 624 and motor 628/drive 629 from contact with fluids. The rotatable spindle 622 can be stainless steel or another material that is corrosion resistant in the presence of water.

The dilution well 625, shown as a test tube-like insert configuration in the FIG., is nested in the rotatable spindle 622 during a dilution and mixing mode and a cleaning high speed spinning mode, but it is a separate removable piece from the system in a preferred embodiment. As shown in the FIG., the spindle 622 and nested dilution well 625 are centered in the chamber 611 relative to imaginary longitudinal axis l. Preferably, the dilution well 625 is a non-wettable material, such as polypropylene, to facilitate water removal from the well 625. In an alternate arrangement, the dilution well 625 can be formed integrally with the spindle 622.

The dilution well 625, as illustrated as a tube insert in the FIG. 6, includes an elongate tapered, hollow cylindrical section 625' having an opening 631 at its upper end 632 and terminating in a closed lower end 633. The tapering or draft angle of the inner surface 625" of the dilution well tube 625 preferably is about 2° such that the tube's inner walls 625" slope slightly outward away from axis l. The taper facilitates creep of the waste fluids out of the bottom of the tube 625 up to the opening 631 during a high speed cleaning mode. A distal tip 634 axially extends from the lower tube end 633 and the tip 634 conformably fits within the gripping recess 624 formed in spindle 622 which effectively forms a grip by the spindle 622 on the dilution well 625. The upper end 632 of the dilution well 625 also has an integral flange 637 which extends radially outward in all directions and it serves as a splash guard that covers and helps protect spindle 622 and motor 628/drive 629 system from fluid contact during the execution of the cleaning mode of the dilution system 610, described in more detail elsewhere herein. The dilution well 625 also includes a plurality of fins or baffles 635 integrally attached to the inner walls 625" of the dilution well 625 which project inward and effectively act as agitators during fluid mixing and dilution. For example, about 3–5 equidistantly spaced fins 635 can be used. The sample and diluent can be filled in the dilution well 625 to a depth that exceeds the height of the fins 635. A dilution well tube 625 having these features can be formed of plastic material by use of conventional plastic molding techniques.

The spindle drive system preferably is capable of adjustment between intermittent and continuous operation modes; the intermittent mode being useful during mixing of the contents in the dilution well. By intermittently energizing the motor 628 in pulses, the fluid contents of the tube are vigorously inter-mixed as encouraged by the fins or baffles provided on the inner sidewalls of the dilution well. On the other hand, the continuous high speed spinning mode is used to clean out the remaining excess fluid contents from the tube after the mixed sample has been withdrawn and transferred to an assay tube for beginning the actual sample analysis. During high speed rotation, left-over fluids in the tube creep up the interior walls of the tube until they reach the mouth of the tube at which point the waste fluids are flung out of the tube and against the inside walls of the dilution well waste chamber. The expelled fluids drain by gravity into the lower basin of the waste chamber and out of a drainage port into waste. Further tube cleaning can be accomplished by the repetitive additions of wash water to the tube during, or followed by, spinning out the wash fluids.

An adjustable spin motor 628 preferably is used that is capable of precision control as to its motor speed and/or capability for relatively brief and instantaneous energization periods. For instance, to effect mixing and dilution of a sample and specimen in the nested dilution well, the motor preferably is "pulsed" to achieve rapid mixing, i.e., the motor is energized for about 100 milliseconds to put the spindle (and dilution well) in rotation, and then de-energized for about 400 milliseconds such that the spindle de-accelerates and stops rapidly due to friction, and then repeating the energization/de-energization cycle at least several times. The dilution well contents are generally pulsed in this manner about 6–8 times; although 3–4 pulses typically has been found adequate for homogenous mixing to be achieved. This scheme effectively causes alternating acceleration/de-acceleration of the dilution well 625 in rotation at low average rpm's such that the fluid contents are well agitated yet without causing the fluids to creep up the inner walls 625" of the dilution well 625 and be prematurely flung out and spilled from the dilution well 625. The pulsed (stop-and-go) tube rotations together with the agitator-like action of the sample tube fins or baffles 635 effectively mixes the sample and diluent held in the dilution well 625 into a homogenous mixture.

A sample pipette, which interacts with but does not form part of the dilution well system per se, can then be used to extract dilute sample from the dilution well 625 and transfer a fraction of the diluted sample to a reaction tube (not shown) for assay. Once the dilute sample is extracted, the dilution well tube 625 is driven in continuous rotation at high speed to cause any residual waste fluids to creep up the inner walls 625" of the dilution well 625 to opening 631 where the fluids are flung out of the tube 625 as indicated by the arrows, which contents are captured within the dilution well waste chamber 611 and drained out of drainage port 636 at the base 621 of waste chamber 611. Wash water can be pipetted into the dilution well 625 through aperture 631 and spun out, once or several times in succession, to further clean the dilution well before introduction, dilution, and mixing of the next sample therein. For most high speed spin removal operations, the tube spin rate will generally range from about 3,000 to about 10,000 rpm. The expelled sample, diluent or other waste fluids drain by gravity into the lower reaches of the chamber 611 and are withdrawn for disposal via drainage port 631.

The sample dilution system of this invention is used as a subsystem of the immunoanalyzer used to perform immunoanalysis on a sample of interest in which the sample can be diluted with diluent or water and mixed into a homogenous solution in the dilution well system of this invention, and then withdrawing a fraction of the mixed sample via pipette and depositing same in a reaction tube (already containing the coated bead) in which a liquid reagent is also added. The mixture of reagent and diluted sample can then be processed according to conventional techniques such as by incubating and agitating the mixture, washing the bead, and then having a substrate (e.g., chemiluminescent) added and incubated for quantitation of analyte (e.g., by reaction tube light output measurement).

When the inventive dilution well system is used in an immunoanalyzer instrument, it is possible to provide user defined dilution factors for the sample prior to analysis and to allow adjustment of the amount of sample dilution in response to prior results where samples give results exceeding the valid measurement limits.

Another aspect of the inventive instrument is a unique bead dispenser device utilized to directly dispense a biomaterial coated bead into a reaction tube with the biomaterial coated bead preserved in a hermetically-sealed environment up until it is actually dispensed into a reaction tube.

Referring to the drawings, and more particularly to FIG. 7A, there is shown a bead dispenser device 700 of the invention useful for supplying, one at a time, beads for heterogenous immunoassay. The dispenser has a track 703, formed as a coiled-ramp-like structure, capable of storing and feeding a plurality of substantially spherical beads (not shown) by effect of gravity to a lower track end 710.

The track 703 serves as a bead support surface and has lateral outer side edges 715 which face sidewall 712 of the chamber 715 in closer proximity than the bead diameter, such as seen in the fragmentary view of FIG. 7A, such that the inner surface of chamber sidewall 712 delimits lateral movement of a bead on the smooth supporting or lower surface 716 of the track 703. The bead support surface 716 extends continuously between an upper track end 709 and the lower track end 710. The track 703 includes a plurality of turns between the upper track end 709 and the lower track end 710. The provision of turns serves to effectively lengthen the distance between the upper track end 709 and the lower track end 710, so that more beads effectively can be stored and supplied along the track 703. The turns must have enough height clearance provided between successive turns to avoid frictional contact with the top of the beads. Also, the track 703 must have enough grade or inclination (angle α in FIG. 7C) provided relative to the horizontal direction (y-direction) to allow the force of gravity to act on the beads to overcome any frictional forces to cause the descent of the column of beads down the track 703 to the lower track end 710.

In a preferred embodiment, the track 703 traces an oval-shaped, spiral path extending from the upper track end 709 to the lower track end 710 winding around a common longitudinal axis (Z-axis in FIG. 7C). The spiral path of the track can also trace a helical path, although an oval shape is preferred as it maximizes track space on an arcuate segment. The spiral path preferably has a constant periodicity between the upper track end 709 and the lower track end 710, although this is not essential, as it is only necessary to ensure adequate height clearance is provided for the beads between successive turns of the spiral path. The track 703 is inclined at an angle α preferably between about 20° to about 60°, and more preferably about 4°, relative to the horizontal direction (y-axis). The selection angle α is a tradeoff between providing enough clearance for the beads between successive turns of the track 710 and ensuring a steep enough grade for rollability of the beads down the track 710. In one embodiment, seen in FIG. 7F and 7A, the uppermost rung of the track 703 has an integral cover 713 having an opening 709' and a backstop 709" to permit top loading of beads. The oval-shape of the track can have about a 15° convergence angle γ (FIG. 7F) towards its smaller radius end. A central opening "c" is left inside the track 703 for attaching the spring finger and for any desired storage of dessicant. The track 703 preferably is formed of molded plastic to provide the structural features disclosed herein in an integral structure.

Returning more specifically to FIG. 7A, an enclosure or chamber 701 hermetically seals and houses the track 703 and comprises a side wall 712 enclosing outer lateral surfaces 715 of the track 703, a cover 713, such as a rigid thermoplastic lid member that is ultrasonically welded to the upper end 714 of the chamber side wall 712 after insertion of the integral track piece 703 within the chamber 701 and loading the beads on the track. The cover 713 hermetically seals the top end of the chamber 701. Side wall 712 can be a continuous oval-shaped or cylindrical shell, such as constituted by thermoplastic material. The chamber 701 also includes a base 714 including upper section 714a and a lower section 714b, which together define a plunger chamber 707. The chamber 701 preferably contains a dessicant material (not shown), such as located within a central open area encircled by the spiral track 703.

A first bead chamber 717 is defined by the upper section 714a of chamber base 714 communicating with the lower track end 710 and the first bead chamber 717 being offset along the plunger chamber 707 relative to a bead exit opening 708 in the lower base section 714b. The base 714 has a mounting flange 725 projecting around the periphery of the bottom of the chamber 700. As best seen in FIG. 7B, opening 710', having a diameter slightly larger than the bead diameters, is provided through upper base section 714a where opening 710' aligns with track end 710 when the spiral track 703 is inserted into chamber 701. The upraised portion of fins "f" project upward from base section 714a to define first bead chamber 717 providing a short bead directing channel between the track end 703 and the opening 710' through upper base section 714a. An opening 710" is formed upper base section 714a adequate to permit insertion and movement of spring finger 718 towards and away from opening 710'. Upper base section 714a is upraised from medial plastic 714' joining the plunger chamber 707 to the chamber sidewall 712. Downward projecting Lower base section 714b and upper base section 714 meet at medial flat plastic 714' to define the plunger chamber 707 compartment.

A plunger 702 is inserted into plunger chamber 707 and is capable of horizontal, reciprocal movement within the plunger chamber 707. As better seen in the side fragmentary view of FIG. 7E, plunger 702 is a rigid material, such as metal, wood, composite, or hard plastic, with, one end, a head 702a and collar portion 702f capable of horizontal movement within the larger recess 722 in chamber base 714, with movement delimited rightward, as seen in FIG. 7A, by flange 719 in the inner wall of plunger chamber 707 of chamber base 714. On the opposite end of plunger 702 there is a distal neck 702e sized to enter flange 723 of base section 714 and to slidably conform to the smaller recess 721 defined in chamber base section 714. The distal neck 702e adjoins shoulder portion 702h via collar portion 702g. The collar portions 702f and 702g have O-rings 705, 706, respectively, fitted thereon. Collar portion 702f, as with medial section 702c, is rectangular in cross section.

Therefore, for the embodiment illustrated, the O-ring 705 fitted on collar 702f assumes a substantially rectangular profile when mounted. The O-ring 706 is circular in profile when mounted on collar 702g.

In the medial section 702c of the plunger, a recess 702d is provided to engage a fingered (free) terminal end 718 of a spring 719, described in greater detail elsewhere herein. The medial section 702c of plunger 702 also has throughhole 702b that is sized large enough to permit unrestricted movement of a single bead 720 (shown in phantom lines in FIG. 7A) to enter, temporarily reside within, and egress the throughhole 702b. As can be understood from an objective of the invention of providing biomaterial coated beads to reaction tubes, it is important that the throughhole 702b have size adequate to accommodate a single bead, but no more, so that each reaction tube receives one and only one bead when ejected from the dispenser device.

The plunger 702 is depicted in its at rest mode, i.e., non-actuated mode, in FIG. 7A, whereby bead exit opening 708 is closed or blocked by a solid portion of the plunger 702. That is, the plunger 702 has a through-hole 702b defining a second bead chamber 702b. This throughhole 702b is normally aligned with the first bead chamber 717 at the lower track end 710 and with a plunger portion 702a concurrently blocking the exit opening 708 via a biasing means.

The biasing means is depicted as a spring 719, such as a molded polypropylene plastic blade-like member, terminating at its lower end in a spring finger 718 that imposes a horizontal bias force on the plunger 702 (rightward in the perspective of FIG. 7A). FIG. 7A shows the side profile of the blade-like spring 719. The spring 719 has a medial portion "m" extending substantially perpendicularly through an opening in the enclosed central portion of the spiraled track 703 relative to the longitudinal axis of the plunger 702 from an upper end 704 attached physically to the track 703, down to the free end 718. The spring finger 718 normally biases the plunger 702 in the position seen in FIG. 7A with horizontal force acting upon the plunger in the direction rightward toward section 702e. The spring means 719 preferably is a discrete plastic elongated piece, such as made of molded polypropylene, which is rigid yet which will tend to flex or spring back to it original position if deflected at its unfixed end. As seen in FIG. 7F, the upper end 704 of spring 719 is mechanically snapped into flanges 704' formed on the inner periphery of central opening "c" inside track 703 in order to mechanically attach the top end 704 of spring 719 to the track 703. The spring 719 is effectively activated during the assembly of the track 703 and spring 719 with the integral chamber 701 and base 714 (housing the plunger 702) in the following manner. During assembly, the plunger 702 is inserted plunger chamber 717. The spring 719 is mechanically snapped into place at its upper end 704 to the track 703. Then, the track 703 and spring 719 are inserted within plunger chamber 707 until the finger latch 718 slides into the notch 702d in the plunger 702 and exerts a rightward pushing force on the plunger 702 (in the perspective of FIG. 7A) until the plunger shoulder 702h abuts flange 723 of plunger chamber 707 via intervening O-ring 706. As shown in FIG. 7A and 7D, the notch 702d has beveling at it upper right end to facilitate entry of finger latch 718 into notch 702d.

In the use of the dispenser device of the invention, exit opening 708 of the dispenser device is positioned directly over a mouth of a reaction tube, then an external force (not shown) is applied to the outer end of section 702e of plunger 702 that is sufficient in magnitude to overcome the internal opposing biasing force of spring 704, so as to displace the plunger 702 leftward (in the view of FIG. 7A) a distance sufficient to align bead chamber 702b of the plunger with exit opening 708, at which point the bead contained and waiting in bead chamber 702b drops by the force of gravity out of the bead chamber, through exit opening 708, and into a reaction tube (or to intermediary means such as tubing used to transport the bead to a reaction tube).

After the bead drops from the plunger 702, the external force is withdrawn and the internal bias forces imposed by spring end 718 acting on abutting portion 702h of plunger 702 causes the plunger 702 to retract to its original position shown in FIG. 7A. Then, as the throughhole 702b re-aligns with the bead chamber 717 at the lower track end 710, the next bead that had been waiting in bead chamber 717 will drop by the force of gravity and by virtue of the weight of the column of beads there behind, into the now vacant throughhole 702b of plunger 702. As the successive bead drops into throughhole 702b, another bead successively moves down to bead chamber 717 at the track end 710 to take its predecessor's place, and so on, for each ejected bead, until the supply of beads is exhausted, the remaining beads deemed expired, or so forth.

To ensure that the chamber 701 is hermetically sealed, O-rings 705 and 706 each are insert molded onto the collar portions 702f and 702g, respectively, of plunger 702 which sealingly engage flanges 724 and 723, respectively, of the plunger chamber 707 of the base section 714. The flange 723 of plunger chamber 707 is inclined at an acute angle of approximately 60° from vertical. By contrast, flange 724 of plunger chamber 707 is inclined at a relatively sharper acute angle of approximately 30° from vertical. As a consequence, overtravel of the plunger 702 is permitted in that a "soft stop" is created at O-ring 706 on the more gentle slope presented by the surface flange 723. Again, the return of plunger 702 after completing a dispensing of a bead is brought about by the bias action of spring 719. In any event, the O-ring 706 contacts flange 723 before O-ring 705 contacts flange 723 by proper dimensioning of the components involved such that O-ring 706 can be squeezed during return of the plunger 702 after dispensing of a bead and removal of actuation force on plunger face 702k. This permits a variable degree of compression of O-ring 706 against the surface of flange 723 until O-ring 705 on the opposite end of the plunger 702 makes a "hard stop" with the steep surface of flange 724. This arrangement of flanges 723 and 724 with O-rings 706 and 705, respectively, prevents sliding friction from occurring between the plunger chamber 707 and the plunger 702.

To impose the normal bias on plunger 702 via spring 719, when plunger 702 is in the closed position depicted in FIG. 7A, the spring 719 is inclined leftward (in perspective of FIG. 7A) at an angle of approximately 3.5° from vertical. This angle is created during assembly of chamber 700 where spring 719 is mechanically attached to the track 703 at its upper end 704 while lower finger 718 is pushed downward such that it slips down inclined wall 702j of plunger notch 702h and ultimately into abutment with the right vertical wall 702i defining plunger notch 702d.

To dispense a bead, a horizontal force is exerted leftward on the right exposed face 702k of plunger distal neck 702e in opposition to and adequate to overcome the opposing normal bias force created in the inclined spring 719. As a result, the plunger 702 horizontally moves (leftward in the perspective of FIG. 7A) to ultimately align the second bead chamber 702b with the exit opening 708 at which point the bead held in plunger receptacle 702b drops out of the plunger 702 and exits the chamber 700 via exit opening 708.

To show the range of movement of the spring 719 during such a dispensing operation, in FIG. 7G, spring 719 has an initial angle $\beta_1$ of approximately 3.5° to the vertical in its at rest position 719a and as attached at its upper end 704 to track 703 before dispensing of a bead is initiated. When the plunger 702 is actuated to dispense a bead, the plunger 702 is deflected leftward (in the perspective of FIG. 7G) a distance such that spring 719 becomes inclined at position 719b at an angle $\beta_2$ of approximately 9° to vertical at which point receptacle 702b is aligned with exit opening 708 and the bead can drop. Once the actuation force is relieved from right end face 702k of plunger 702, the flexure intrinsic to the plastic spring 719 will cause it to automatically return back to its initial angle $\beta_1$ of approximately 3.5° to the vertical as its at rest position 719a.

The bead dispenser of this invention thus can serve the following functions:

a) to protect the beads contained therein from environmentally induced damage;

b) to package the beads in a fashion convenient for operator access and handling;

c) to facilitate the dispensing of a single bead into each reaction tube as needed;

d) to provide the necessary space for identification and product labeling; and e) to enable visual estimation of bead inventory by the operator.

To provide the ability to perform a wide variety of different types of immunoassays on board a common immunoassay analyzer, the bead dispenser of this invention is effectively used in combination with a plurality of like bead dispenser devices useful for supplying beads, one at a time, for heterogenous immunoassay to a common location for addition to reaction tubes. Each such dispenser device comprising the structure described herein and any given dispenser device being loaded with beads all having the same biomaterial coated thereupon, with the proviso that at least one or more of the bead dispensers stores a different type of biomaterial as coated on its beads as compared to its cohort dispenser devices.

The rotatable bead carousel 203, such as a rotatable platform, is used to accommodate a large number of bead dispensers of the invention, e.g., up to about 24 or even more, each dispenser being capable of holding large numbers of beads. For instance, the bead dispensers of the present invention typically are loaded with about 200 beads. The entire carousel preferably is housed within a dehumidified chamber maintained at about 10% relative humidity.

The bead carousel platform holding the bead dispensing devices can be rotated 360° to allow any given dispenser device to be moved by an identifying and selecting means to a bead loading station where the carousel passes over and intersects (in a top view) the track of a reaction tube loading chain.

As explained above, it is useful and practical to provide means for identifying each of the plurality of dispenser devices, such as by a readable bar code associated with each dispenser device, and the system further comprising a selecting means, such as including a bar code reader, for identifying and selecting from among the plurality of dispenser devices. For example, vertically oriented bar codes can be applied to each bead dispenser making it accessible to reading by a dedicated CCD bar code reader. The system also includes means electromechanically activatable for displacing a plunger of a selected dispenser device as positioned at the bead loading station over a reaction tube to cause one bead to drop from said exit opening into the mouth of the reaction tube.

In conjunction therewith, there will also be means provided for identifying a reaction tube and its intended analyte contents and relating the reaction tube back to the related dispenser device having a given biomaterial bound to a surface of the beads. Such system can include a tube transport means capable of moving the identifiable reaction tube to a bead loading station, relating the identified reaction tube to a related dispenser device having a given biomaterial bound to a surface of the beads as needed to conduct the assay desired for the sample of interest subsequently to be added to the reaction tube. Once the related dispenser device and reaction tube are aligned at the bead loading station, then a bead is ejected from the related bead dispenser into the reaction tube, and then the reaction tube is conveyed with the bead out of the bead loading station to additional stations to conduct the immunoassay itself (e.g., sample and reagent addition, incubation, washing, quantitation, and so forth), and the next reaction tube is brought to the bead loading station, and the operation repeated for all reaction tubes to be analyzed.

In a preferred mode of using the bead dispensing system of this invention, when the analyzer 10 first encounters a bead dispenser of a particular test type and serial number, the computer 12 will initialize an internal database to reflect the initial number of beads in that particular bead dispenser. Then each time a bead is dispensed from the bead dispenser, this internal counter will be decremented. Whenever a new run is initiated, the computer 12 will verify that sufficient fresh (unexpired) beads for each test ordered are available on-board. If not, operators will be advised via VDT display or audible warning, and so forth, to add another suitable bead dispenser before leaving the instrument 10 unattended.

Further, when the bead carousel 203 is accessed, the analyzer preferably should have support software to verify the availability of all required information. If any is lacking, e.g., the bar code is unreadable or there is an absence of information about which tests to run or how to run them, the operator will be alerted immediately. As such, the analyzer can be programmed to proceed to process all on-board specimens before requiring further attention. Regarding possible test specific problems, if no beads were dispensed, an additional attempt will be made to do so. If two beads were dispensed, the bead dispenser's bead count will be decremented by two, a new reaction tube drawn and an additional attempt made to dispense a bead. If the second attempt fails, operators are alerted immediately of the problem via both on-screen and audible alarms. Meanwhile, the analyzer can be programmed to continue to process other test types while waiting operator intervention. As to possible hardware problems, such as bead carousel component failures, jams, excessive humidity in the chamber, and so forth, operators are alerted immediately of such problems via both on-screen and audible alarms. Until the operator intervenes, sampling operations will be suspended, but the tube processor operations can programmed to continue.

According to another aspect of the invention, there is an improved tube washing system 214 (FIG. 2) provided with a high speed spinning station having an chuck housed within and surrounded by a waste chamber, where the waste chamber serves as a receptacle for collecting and draining wash water fluid spun out of a tube.

Referring again to the drawings, and more particularly to FIG. 8A, there generally is shown a tube washing system 810 provided with a high speed spinning station 820 having an angled, grooved chuck 822 housed within and surrounded by a waste chamber 823. Further details on the configuration of chuck 822 will be developed hereinafter where suitable. In FIG. 8A, the high speed spinning station 820 is shown in its nonengaged position relative to tube 840. When engaged, such as shown in FIG. 8E, the waste chamber 823 serves as a receptacle for collecting and draining wash water fluid spun out of a tube 840. The waste chamber 823 is an enclosure defined by an upper surface 824, side wall 825, and a bottom surface 826 having an arcuate shape curving inward and upward near its center to define an aperture 828 bounded by upward projection 821. The aperture 828 has a size selected permit entry of tube 840. The port 827 communicates with a lower end of the chamber 823 to provide a means of drainage of wash water and other fluids expelled from the tube 840 during centrifugation and captured in waste chamber 823. As bottom surface 826 has upward curving projections 821, wash fluid that is expelled from a tube during spinning will strike chamber walls 824 and 825 and then drain by gravity out of port 827 without being able to climb up and over projections 821 at the bottom surface of the chamber 823. Therefore, wash fluid will not seep out of a small gap provided between tube 840 and the closely confronting, but noncontacting, inward surfaces 821a of projections 821. The opening 828 defined by chamber projections 821 is sized to provide a small circumferential gap "G", e.g., about $12/1000$ inch clearance, between the inner surfaces of projections 821 and the continuous tube flange 846.

As more easily seen in FIG. 8G, the chuck 822 preferably is a bevel gear has a body portion defined by an upper surface 822b of generally hemispherical-shape merging into upright stem 822d, and a grooved bottom surface 822c. As best seen in FIG. 8F, the bevel gear 822 has alternating grooves or slots 822a and teeth 822e disposed around the entire circumference of bottom surface 822c. As seen in FIG. 8G, the series of spaced apart teeth 822e and intervening grooves 822a angle up to hemispherical portion 822b at an angle, preferably an angle of about 45°. Chuck 822 also has a central throughhole "c" capable of receiving and allowing a pipette to be passed through the chuck. The chuck 822 also is formed of a rigid material, such as metal. The chuck 822 is mounted in shaft 829 for rotation and the chuck 822 distends through the top surface 824 to reside inside the waste chamber 823. The drive shaft 829 is sealed with an O-ring 830, and bearings 832 are provided between drive shaft 829 and support frame 831. The drive shaft 829 is driven to rotate about axis z—z by a spin motor (not shown).

A pipette 833 extends through drive shaft 829 and the center of chuck 822 and its dispensing tip 834 emerges from the bottom of chuck 822 a distance sufficient to permit the tip 834 to enter a tube 840 (once lifted into chamber 823 as seen in FIG. 8E) without closely approaching or contacting the bead support 841. A solenoid wash pump (not shown) controllably delivers wash water volumes to pipette 833. The pipette 833 does not spin with chuck 822 due to the provision of bushing 857 around pipette 833. The bushing 857 can spin while maintaining pipette 833 in a centered non-spinning position.

The tube 840 to be washed has at least one projection or ridge 843 (best seen in FIG. 8B and FIG. 8C) upstanding from the inner surface 844 of the tube. Preferably, the ridge 843 gradually tapers in height and width downward from the upper rim 858 of the mouth 845 of tube 840 and disappears on the inner surface 844 as it approaches the inner bottom of the tube 840. The ridge(s) 843, at the rim area 858, is sized in inward projection and width dimensions sufficient to permit sliding of the ridge(s) 843 into a groove(s) 822a of chuck 822 and its nesting between two adjoining chuck teeth 822e. The inter-fit of the ridge 843 and chuck groove 822a preferably should be provided with close clearances as loose fits may cause wear on the ridges 843 or chuck teeth 822e.

For example, in the illustrations of FIGS. 8B and 8C, three ridges 843 have been provided on the inner surface 844 of test tube 840, which ridges can be nested between three pairs of teeth in chuck 822 to provide means of temporarily physically and mechanically interlocking the tube 840 and chuck 822 when the tube 840 is engaged (lifted into) chamber 823 such as shown in FIG. 8E. Preferably a plurality of ridges 843, e.g. three or more, will be formed on the inner side 844 of the tube 840 as equidistantly spaced around the inner circumference of the tube 840. The ridges 843 preferably will have a draft angle of about 0.5°, while the tube surface 844 has a draft angle of about 2° to prevent nesting of the tube in a bulk hopper.

The number of ridges 843 will be less than the total number of grooves 822a provided in chuck 822. Therefore, at least one, and preferably a plurality, of grooves 822a will remain unobstructed by any ridge 843 of tube 840 during tube spinning, and thus remain available as escape paths for wash fluids being expelled from the tube 840 during spinning within the waste chamber 823.

The tube 840, at its bottom end, preferably is provided with a continuous circular sleeve 847 extending downward and defining a recess 849 in its bottom surface to permit handling by a lifting means holder, described in greater detail hereinafter. The tube 840, at its top end, preferably has a continuous flange means 846 provided on its outer side wall. The tube 840 is supported and oriented for alignment of tube ridges 843 with chuck grooves 822a by tube conveyor chain link 848 when the tube 840 is nonengaged (nonlifted) relative to the high speed spinning station 820, such as shown in FIG. 8A.

To form the ridges 843 and continuous flange 846 integral with reaction tube 840, reaction tube 840 can be injection molded with styrene-butadiene copolymer, such as "KR03", commercially available from Phillips 66 Co, Bartlesville, Okla. 74004.

The reaction tube 840 is lifted (and retracted) vertically along the z—z axis direction via tube elevating means 850, such as shown in FIG. 8A. Tube elevating means 850 includes a tube holder 851 which holds and retains tube 840 during lift of tube 840 into waste chamber 823. As shown in FIG. 8H, the tube holder 851 is a hollow metal tube 852 divided at its upper half by four slots "s" extending from the top end "t" to about halfway down the length of tube 852. This defines four 90° quadrants at the top end "t" of tube 852 and the tube is flanged or hooked by bending outward at top end "t". The tube 852 preferably is beryllium-copper alloy, which provides good spring-like flexure properties. As seen in FIG. 8E, the flanged top "t" of tube 852 interfits recess 849 of the bottom of the tube 840, such that posts 847 of tube 840 can slide over the outer flanged periphery at the top "t" the tube 852 with continuous circular tube holder sleeve 853 sliding in opposition over the outer sides of the tube posts 847. The flanged portion "t" of tube 852 is slightly oversized relative to recess 849 in tube 840 for positive retraction. The tube elevating means 850 includes bearings 854 permitting free rotation of the tube holder 851 relative to transfer block 856. The tube elevating means 850 further includes a reciprocal shaft 855, which is vertically moveable in the z—z axis direction, where the shaft 855 is connected to a lift motor (not shown). The lift motor, when actuated, will drive the shaft 855 vertically upward to interfit tube holder 851 with the bottom of tube 840, as supported and oriented by a chain link of a tube conveyor 848, and continue to lift the tube 840 to a height until it enters waste chamber 823 and tube ridge(s) 843 slides into and mate with chuck groove(s) 822a. At this point, as shown in FIG. 8E, the tube 840 is engaged with high speed spinning station for washing and spinning. The flanges 846 of the tube 840 present an outer profile diameter that is less than the diameter of aperture 828 defined by bottom surface 826 of the waste chamber 823.

Once the tube 840 is so elevated into the chamber 823 effective to mechanically interlock with the chuck 822 via mating of tube ridge(s) 843 and chuck groove(s) 822a, the tube 840 is rotated on its vertical axes z—z by driving the chuck 822 in rotation while the tube is supported at the bottom of the tube (847, 849) via freely rotatable holder 851 which rotates as dictated by the movement of the chuck. During rotation, fluids are expelled from the tube 840 into the waste chamber 823 through the grooves 822a in the chuck 822, while allowing the retention of any immunoreceptive bead 841 held within the tube 840. For most wash applications, the tube spin rate will generally range from about 3,000 to about 10,000 rpm.

When rotation ceases, the expelled waste fluids drain by gravity into the lower basin 826a of the waste chamber 823 and are withdrawn for disposal via drainage port 827. Washing can be accomplished by the addition of water to the tube 840 during, or followed by, centrifugation. Wash water is added to the assay tube 840 via a solenoid wash pump (not shown) delivering volumes of wash water to pipette 833 which pipettes the volumes of water straight down into assay tube 840. Although not particularly limited to such, in a preferred operation, multiple 400 $\mu$L volumes of water (e.g. four) are pipetted into the assay tube 840. After each addition, the wash water is almost instantaneously removed after washing the inert support 841 with the bound biomaterial by high speed rotation of the tube 840.

Once the washing and centrifugation are completed for a given tube 840, the tube can be lowered via the tube elevating means 850 by retracting its shaft 855 with the tube ridge(s) 843 sliding back out of the chuck groove(s) 822a and the tube 840 eventually clearing the waste chamber 823.

After washing, the reaction (or assay) tube 840 and inert support 841 will be free of unbound labeled reagent so that only bound labeled reagent will be detected.

After completion of the washing operation, the washed tubes are transferred to a detection station for quantification of the analyte of interest, such as by chemiluminescent techniques described in U.S. Pat. No. 5,316,726, which is incorporated herein by reference.

The use of the tube washing system 810, such as shown in FIG. 8E, greatly facilitates the washing operation required in performing an immunoasssay and represents a significant improvement over the use of aspiration equipment in an automated immunoassay analyzer environment. In particular, removal of the sample and wash fluid in the above-described manner allows the wash operation to be performed rapidly and facilely.

While the invention has been described in terms of its preferred embodiments, those skilled in the art will recognize that the invention can be practiced with modification within the spirit and scope of the appended claims.

What is claimed is:

1. An automated immunoassay analyzer, comprising: an instrument which includes
    (I) means for receiving a plurality of sample tubes containing a fluid sample to be assayed;
    (II) means for supplying a plurality of reaction tubes in which an assay on said samples can be performed;

(III) inert support and dispensing means for receiving a plurality of inert support dispensing packs each storing a single type of biomaterial-coated inert support, said biomaterial capable of selectively binding an analyte of interest in a sample, and said dispensing packs capable of storing and dispensing said supports, individually, into a reaction tube at a support dispensing station, whereby a plurality of different biomaterial coated supports stored on-board said analyzer can be selected from for addition to said reaction tube for performing a particular assay in said reaction tube, said inert support supply and dispensing means comprising (1) a plurality of bead dispenser devices supported on a common bead dispenser device carousel capable of rotation, wherein each dispenser device comprises
   (a) a track capable of storing and feeding a plurality of substantially spherical beads by effect of gravity to a lower track end,
   (b) an enclosure sealingly housing said track comprising
      a side wall enclosing outer lateral surfaces of said track,
      a cover sealingly enclosing an upper track end of said track and upper end of said side wall, and
      a base including upper and lower sections defining a plunger chamber, and a first bead chamber defined in said upper section communicating with said lower track end and said first bead chamber being offset along said plunger chamber relative to a bead exit opening in said lower section,
   c) a plunger sealingly provided in said plunger chamber and being capable of horizontal reciprocal movement within said plunger chamber, said plunger having a throughhole defining a second bead chamber normally aligned with said first bead chamber at said lower track end and with a plunger portion concurrently blocking said exit opening via a biasing means imposing a normal horizontal bias force on said plunger, wherein when a horizontal force is exerted in opposition to and adequate to overcome said normal bias force, said plunger being capable of horizontal movement to align said second bead chamber with said exit opening, said normal horizontal biasing force of said biasing means capable of horizontally moving said plunger effective to reblock said exit opening upon removal of said opposing force, and wherein said plunger further comprises first and second resilient rings spaced apart and seated on respective first and second collar portions of said plunger, and said plunger chamber having first and second flanges capable of sealingly engaging said first and second resilient sealing rings, respectively, where said first flange is located between said exit opening and said first bead chamber and said second flange is located between said biasing means and a distal end of said plunger at which said horizontal force is exerted, and
(2) identifying means for identifying each of said bead dispenser devices;

(IV) means for receiving a plurality of reagent storage packs capable of storing and permitting reagent withdrawal, in a self-sealing manner, whereby a plurality of different reagents stored on-board said analyzer can be selected from for addition to said reaction tube for performing a particular assay in said reaction tube;

(V) means for pipetting sample and means for pipetting reagent into a support-containing reaction tube at a reaction tube pipetting station;

(VI) an incubating station for incubating reaction tubes received from said reaction tube pipetting station containing sample, reagent and inert support;

(VII) a washing station for washing bound biomaterial in said reaction tube after said reaction tubes have been incubated at said incubating station;

(VIII) a detection station for detecting a quantity of analyte bound to said biomaterial in said reaction tubes after said reaction tubes have been washed at said washing station, said detection station producing a signal proportional to the quantity of analyte for each reaction tube;

(IX) a reaction tube transport pathway connecting, in this sequence, said reaction tube supply means, said inert support supply and dispensing means, said reaction tube pipetting station, said incubating station, said washing station and said detection station;

(X) means for identifying said sample tubes, said reagent packs, and said inert support dispensing packs on-board the analyzer;

(XI) control means for automatic controlling of various components of said analyzer in a coordinated manner and being capable of executing assay selection orders for a given sample by selecting and coordinating the introduction of a particular type of reagent and particular type of biomaterial-coated inert support effective to perform a particular requested assay on said sample in a reaction tube; and (XII) means for determining and displaying and/or recording the concentration of analyte in a particular sample based on said signal produced and detected at said detection station.

2. The automated immunoassay analyzer of claim 1, wherein each of said rotatable sample tube carousel, said rotatable reagent pack carousel, and said rotatable inert support pack carousel, are associated with a bar code reader, whereby said control means can controllably track and advance said sample tubes to said sample pipetting means, said reagent packs to said reagent pipetting means, and said inert support dispensing packs to said inert support dispensing station.

3. The automated immunoassay analyzer of claim 1, wherein said control means includes a computer connected to said analyzer via data communication lines.

4. The automated immunoassay analyzer of claim 3, wherein said computer is connected via data communication lines to (a) a display means which visually displays operator commands and data collected from the instrument, and (b) a keyboard allowing input of patient information associated with test samples.

5. The automated immunoassay analyzer of claim 3, wherein said analyzer includes microprocessing means on-board the analyzer directing operation of said analyzer.

6. The automated immunoassay analyzer of claim 1, wherein said detection station includes a means for detecting light.

7. The automated immunoassay analyzer of claim 6, wherein said means for detecting light is a photomultiplier tube.

8. The automated immunoassay analyzer of claim 1, wherein said sample tube receiving means comprises:
a rotatable sample rack carousel supporting at least one sample container rack, said at least one sample container rack comprising:

a base;

a sample container holder sleeve, including:
- a cylindrical-shaped shell defining a sidewall structure, an upper opening, and an interior space, and said shell being oriented vertically relative to said base and including a vertically extending slot opening in said sidewall structure, and
- a plurality of sample container gripping means attached to said sidewall structure each having at least one projection tab resiliently urged inward, said projection tabs capable of gripping a sidewall of a sample container inserted into said shell to maintain said sample container in a centered, upright orientation.

9. An automated immunoassay analyzer, comprising: an instrument which includes (I) means for receiving a plurality of sample tubes containing a fluid sample to be assayed;

(II) means for supplying a plurality of reaction tubes in which an assay on said samples can be performed;

(III) insert support and dispensing means for receiving a plurality of inert support dispensing packs each storing a single type of biomaterial-coated inert support, said biomaterial capable of selectively binding an analyte of interest in a sample, and said dispensing packs capable of storing and dispensing said supports, individually, into a reaction tube at a support dispensing station, whereby a plurality of different biomaterial coated supports stored on-board said analyzer can be selected from for addition to said reaction tube for performing a particular assay in said reaction tube;

(IV) means for receiving a plurality of reagent storage packs capable of storing and permitting reagent withdrawal, in a self-sealing manner, whereby a plurality of different reagents stored on-board said analyzer can be selected from for addition to said reaction tube for performing a particular assay in said reaction tube, said means for receiving a plurality of reagent storage packs comprising
- a plurality of reagent containers removably fitted into a common reagent carousel, each said reagent container comprising
  - a vessel having a plurality of separate compartments defined by sidewalls and a cover as an upper surface, each compartment having an opening in said upper surface;
  - a self-sealing lid attached to the exterior of a sidewall of said vessel, comprising
    - a first arm confronting said upper surface of said vessel, said first arm supporting a plurality of caps interspaced by openings extending through said arm, said first arm capable of reciprocal movement over said upper surface of said vessel to permit covering and uncovering of said compartment openings by said caps,
    - a second arm confronting said exterior sidewall of said vessel, said second arm having a lower end attached to said sidewall of said vessel and an upper end connected to said first arm via a first hinge,
    - guide means maintaining reciprocal displacement of said first arm along a single horizontal line of movement,
    - whereby said first arm of said lid is subject to a normal bias force created by said second arm whereby said plurality of caps normally covers said compartment openings, wherein when a horizontal external force is exerted in opposition to and adequate to exceed said normal bias force said first arm being capable of horizontal displacement adequate to uncover said caps from said compartment openings, and upon removal of said horizontal external forces said normal bias force acting on said first arm of said lid to re-cover said compartment openings with said caps;

(V) means for pipetting sample and means for pipetting reagent into a support-containing reaction tube at a reaction tube pipetting station;

(VI) an incubating station for incubating reaction tubes received from said reaction tube pipetting station containing sample, reagent and inert support;

(VII) a washing station for washing bound biomaterial in said reaction tube after said reaction tubes have been incubated at said incubating station;

(VIII) a detection station for detecting a quantity of analyte bound to said biomaterial in said reaction tubes after said reaction tubes have been washed at said washing station, said detection station producing a signal proportional to the quantity of analyte for each reaction tube;

(IX) a reaction tube transport pathway connecting, in this sequence, said reaction tube supply means, said inert support supply and dispensing means, said reaction tube pipetting station, said incubating station, said washing station and said detection station;

(X) means for identifying said sample tubes, said reagent packs, and said inert support dispensing packs on-board the analyzer;

(XI) control means for automatic controlling of various components of said analyzer in a coordinated manner and being capable of executing assay selection orders for a given sample by selecting and coordinating the introduction of a particular type of reagent and particular type of biomaterial-coated inert support effective to perform a particular requested assay on said sample in a reaction tube; and (XII) means for determining and displaying and/or recording the concentration of analyte in a particular sample based on said signal produced and detected at said detection station.

10. An automated immunoassay analyzer, comprising: an instrument which includes (I) means for receiving a plurality of sample tubes containing a fluid sample to be assayed;

(II) means for supplying a plurality of reaction tubes in which an assay on said samples can be performed;

(III) insert support and dispensing means for receiving a plurality of inert support dispensing packs each storing a single type of biomaterial-coated inert support, said biomaterial capable of selectively binding an analyte of interest in a sample, and said dispensing packs capable of storing and dispensing said supports, individually, into a reaction tube at a support dispensing station, whereby a plurality of different biomaterial coated supports stored on-board said analyzer can be selected from for addition to said reaction tube for performing a particular assay in said reaction tube;

(IV) means for receiving a plurality of reagent storage packs capable of storing and permitting reagent withdrawal, in a self-sealing manner, whereby a plurality of different reagents stored on-board said analyzer can be selected from for addition to said reaction tube for performing a particular assay in said reaction tube;

(V) means for pipetting sample and means for pipetting reagent into a support-containing reaction tube at a reaction tube pipetting station;

(VI) an incubating station for incubating reaction tubes received from said reaction tube pipetting station containing sample, reagent and inert support;

(VII) a washing station for washing bound biomaterial in said reaction tube after said reaction tubes have been incubated at said incubating stations, said washing station comprises
a tube spinning station having
a rotatable chuck, wherein said chuck comprises a body portion and a plurality of spaced apart teeth defining intervening grooves extending through said body portion with at least one of said grooves permitting passage of fluid through said body portion and at least one other of said grooves providing means to receive and mechanically connect a projection on an open end of a tube,
a fluid waste chamber housing said chuck, and said waste chamber comprises means to collect and drain fluid, and an aperture defined in a lower side of said chamber having a size effective to permit entry of said tube into said chamber,
a pipette for dispensing wash water into said tube, said pipette located centrally within said chuck, drive means to rotate said chuck, and
a tube elevating means located beneath said tube spinning station, said tube elevating means comprising a freely rotatable tube holder, and lifting means provided to vertically move said tube holder towards and away from said chuck;

(VIII) a detection station for detecting a quantity of analyte bound to said biomaterial in said reaction tubes after said reaction tubes have been washed at said washing station, said detection station producing a signal proportional to the quantity of analyte for each reaction tube;

(IX) a reaction tube transport pathway connecting, in this sequence, said reaction tube supply means, said inert support supply and dispensing means, said reaction tube pipetting station, said incubating station, said washing station and said detection station;

(X) means for identifying said sample tubes said reagent packs, and said inert support dispensing packs on-board the analyzer;

(XI) control means for automatic controlling of various components of said analyzer in a coordinated manner and being capable of executing assay selection orders for a given sample by selecting and coordinating the introduction of a particular type of reagent and particular type of biomaterial-coated inert support effective to perform a particular requested assay on said sample in a reaction tube; and (XII) means for determining and displaying and/or recording the concentration of analyte in a particular sample based on said signal produced and detected at said detection station.

11. The automated immunoassay analyzer of claim 1, wherein said means for receiving a plurality of sample tubes containing a fluid sample to be assayed further receives tubes containing diluent material, and said analyzer further comprising a sample dilution station, comprising: (a) a dilution tube well capable of receiving sample and diluent via said sample pipetting means, and (b) means on-board the analyzer to rotate said dilution tube well sufficient to form a homogenous mixture, wherein said sample pipetting means being capable of transferring portions of said mixture to reaction pipetting station, and said dilution well rotation means capable of high speed rotation of said dilution tube well to eliminate excess mixture fluid, and (c) means on-board the analyzer for catching said mixture fluid expelled during said high speed rotation.

12. The automated immunoassay analyzer of claim 11, wherein said sample dilution station further comprises, in combination:
a dilution well waste chamber defined by (a) a chamber body having inner sidewalls and a bottom defining a space, wherein said bottom includes a drainage port and a centrally located opening, and (b) a dilution well cover having a central hole, said dilution well cover being removably fitted upon said chamber body to cover said space;
a dilution well, including:
an elongated hollow cylinder having inside walls, an upper end and a lower end, said upper end having an opening and said lower end having a plurality of inward projecting fins integral with said inside tube walls;
a dilution well spinning means, including:
a holding means for conformably receiving and supporting said dilution well,
a drive means capable of effecting rotation of said holding means and said dilution well, wherein said drive means includes a motor, and said holding means comprises a spindle where said motor controllably drives said spindle in rotation, and said spindle comprising a hollow sleeve defining a recess sized to permit nesting of said dilution well inside said spindle whereby said dilution well is capable of traveling in rotation with said spindle.

13. The automated immunoassay analyzer of claim 1, wherein said first collar is a rectangular-shaped recess in said plunger and said first resilient ring comprises a rectangular-shaped O-ring, and said second collar is circular-shaped recess in said plunger and said second resilient ring comprises a circular-shaped O-ring.

14. The automated immunoassay analyzer of claim 1, wherein during said blocking of said exit opening by said plunger portion, said first resilient sealing ring sealingly confronts said first flange of said plunger chamber inclined at a first acute inclination angle from vertical, and said second resilient sealing ring sealingly confronts said second flange of said plunger chamber inclined at a second acute inclination angle from vertical, wherein said second inclination angle is smaller in inclination than said first inclination angle an amount effective to permit said second resilient sealing ring to variably compress until said first resilient sealing ring stops on said first flange.

15. An automated immunoassay analyzer, comprising:
an instrument which includes
(I) means for receiving a plurality of sample tubes containing a fluid sample to be assayed;
(II) means for supplying a plurality of reaction tubes in which an assay on said samples can be performed;
(III) insert support and dispensing means for receiving a plurality of inert support dispensing packs each storing a single type of biomaterial-coated inert support, said biomaterial capable of selectively binding an analyte of interest in a sample, and said dispensing packs capable of storing and dispensing said supports, individually, into a reaction tube at a support dispensing station, whereby a plurality of different biomaterial coated supports stored on-board said analyzer can be selected from for addition to said reaction tube for performing a particular assay in said reaction tube, said inert support supply and dispensing means comprises (1) a plurality of bead dispenser devices supported on a common bead dispenser device carousel capable of rotation, wherein each dispenser device comprises
   (a) a track capable of storing and feeding a plurality of substantially spherical beads by effect of gravity to a lower track end,
   (b) an enclosure sealingly housing said track, comprising
      a side wall enclosing outer lateral surfaces of said track,
      a cover sealingly enclosing an upper track end of said track and upper end of said side wall, and
      a base including upper and lower sections defining a plunger chamber, and a first bead chamber defined in said upper section communicating with said lower track end and said first bead chamber being offset along said plunger chamber relative to a bead exit opening in said lower section,
   c) a plunger sealing provided in said plunger chamber and being capable of horizontal reciprocal movement within said plunger chamber, said plunger having a throughhole defining a second bead chamber normally aligned with said first bead chamber at said lower track end and with a plunger portion concurrently blocking said exit opening via a biasing means imposing a normal horizontal bias force on said plunger, wherein when a horizontal force is exerted in opposition to and adequate to overcome said normal horizontal bias force said plunger being capable of horizontal movement to align said second bead chamber with said exit opening, said normal biasing force of said biasing means capable of horizontally moving said plunger effective to reblock said exit opening upon removal of said opposing force, and wherein said plunger further comprises a notch receiving a fingered free end of said horizontal biasing means, said horizontal biasing means having an upper end attached to said track and a medial portion extending substantially perpendicularly relative to a longitudinal axis of the plunger to terminate in said free end, and (2) identifying means for identifying each of said bead dispenser devices;

(IV) means for receiving a plurality of reagent storage packs capable of storing and permitting reagent withdrawal, in a self-sealing manner, whereby a plurality of different reagents stored on-board said analyzer can be selected from for addition to said reaction tube for performing a particular assay in said reaction tube;

(V) means for pipetting sample and means for pipetting reagent into a support-containing reaction tube at a reaction tube pipetting station;

(VI) an incubating station for incubating reaction tubes received from said reaction tube pipetting station containing sample, reagent and inert support;

(VII) a washing station for washing bound biomaterial in said reaction tube after said reaction tubes have been incubated at said incubating station;

(VIII) a detection station for detecting a quantity of analyte bound to said biomaterial in said reaction tubes after said reaction tubes have been washed at said washing station, said detection station producing a signal proportional to the quantity of analyte for each reaction tube;

(IX) a reaction tube transport pathway connecting, in this sequence, said reaction tube supply means, said inert support supply and dispensing means, said reaction tube pipetting station, said incubating station, said washing station and said detection station;

(X) means for identifying said sample tubes, said reagent packs, and said inert support dispensing packs on-board the analyzer;

(XI) control means for automatic controlling of various components of said analyzer in a coordinated manner and being capable of executing assay selection orders for a given sample by selecting and coordinating the introduction of a particular type of reagent and particular type of biomaterial-coated inert support effective to perform a particular requested assay on said sample in a reaction tube; and (XII) means for determining and displaying and/or recording the concentration of analyte in a particular sample based on said signal produced and detected at said detection station.

16. An automated immunoassay analyzer, comprising:
an instrument which includes
(I) means for receiving a plurality of sample tubes containing a fluid sample to be assayed, wherein said sample tube receiving means comprises at least one sample tube rack supported on a rotatable sample tube carousel;
(II) means for supplying a plurality of reaction tubes in which an assay on said samples can be performed;
(III) insert support and dispensing means comprising a rotatable inert support pack carousel for receiving a plurality of inert support dispensing packs each storing a single type of biomaterial-coated inert support, said biomaterial capable of selectively binding an analyte of interest in a sample, and said dispensing packs capable of storing and dispensing said supports, individually, into a reaction tube at a support dispensing station, whereby a plurality of different biomaterial coated supports stored on-board said analyzer can be selected from for addition to said reaction tube for performing a particular assay in said reaction tube;
(IV) means comprising a rotatable reagent pack carousel for receiving a plurality of reagent storage packs capable of storing and permitting reagent withdrawal, in a self-sealing manner, whereby a plurality of different reagents stored on-board said analyzer can be selected from for addition to said reaction tube for performing a particular assay in said reaction tube, and wherein said reagent pack carousel is located concentrically within said sample tube carousel, and said sample tube carousel, and said inert support pack carousel are independently rotatable relative to each other, said means for receiving a plurality of reagent storage packs comprising
a plurality of reagent containers removably fitted into a common reagent carousel, each said reagent container comprising
a vessel having a plurality of separate compartments defined by sidewalls and a cover as an upper surface, each compartment having an opening in said upper surface;

a self-sealing lid attached to the exterior of a sidewall of said vessel, comprising
a first arm confronting said upper surface of said vessel, said first arm supporting a plurality of caps interspaced by openings extending through said arm, said first arm capable of reciprocal movement over said upper surface of said vessel to permit covering and uncovering of said compartment openings by said caps,
a second arm confronting said exterior sidewall of said vessel, said second arm having a lower end attached to said sidewall of said vessel and an upper end connected to said first arm via a first hinge,
guide means maintaining reciprocal displacement of said first arm along a single horizontal line of movement,
whereby said first arm of said lid is subject to a normal bias force created by said second arm whereby said plurality of caps normally covers said compartment openings, wherein when a horizontal external force is exerted in opposition to and adequate to exceed said normal bias force said first arm being capable of horizontal displacement adequate to uncover said caps from said compartment openings, and upon removal of said horizontal external forces said normal bias force acting on said first arm of said lid to re-cover said compartment openings with said caps;

(V) means for pipetting sample and means for pipetting reagent into a support-containing reaction tube at a reaction tube pipetting station;

(VI) an incubating station for incubating reaction tubes received from said reaction tube pipetting station containing sample, reagent and inert support;

(VII) a washing station for washing bound biomaterial in said reaction tube after said reaction tubes have been incubated at said incubating station;

(VIII) a detection station for detecting a quantity of analyte bound to said biomaterial in said reaction tubes after said reaction tubes have been washed at said washing station, said detection station producing a signal proportional to the quantity of analyte for each reaction tube;

(IX) a reaction tube transport pathway connecting, in this sequence, said reaction tube supply means, said inert support supply and dispensing means, said reaction tube pipetting station, said incubating station, said washing station and said detection station;

(X) means for identifying said sample tubes, said reagent storage packs, and said inert support dispensing packs on-board the analyzer;

(XI) control means for automatic controlling of various components of said analyzer in a coordinated manner and being capable of executing assay selection orders for a given sample by selecting and coordinating the introduction of a particular type of reagent and particular type of biomaterial-coated inert support effective to perform a particular requested assay on said sample in a reaction tube; and (XII) means for determining, and displaying and/or recording the concentration of analyte in a particular sample based on said signal produced and detected at said detection station.

17. An automated immunoassay analyzer, comprising:
an instrument which includes (I) means for receiving a plurality of sample tubes containing a fluid sample to be assayed, wherein said sample tube receiving means comprises at least one sample tube rack supported on a rotatable sample tube carousel;

(II) means for supplying a plurality of reaction tubes in which an assay on said samples can be performed;

(III) insert support and dispensing means comprising a rotatable inert support pack carousel for receiving a plurality of inert support dispensing packs each storing a single type of biomaterial-coated inert support, said biomaterial capable of selectively binding an analyte of interest in a sample, and said dispensing packs capable of storing and dispensing said supports, individually, into a reaction tube at a support dispensing station, whereby a plurality of different biomaterial coated supports stored on-board said analyzer can be selected from for addition to said reaction tube for performing a particular assay in said reaction tube, said inert support supply and dispensing means comprises (1) a plurality of bead dispenser devices supported on a common bead dispenser device carousel capable of rotation, wherein each dispenser device comprises
    (a) a track capable of storing and feeding a plurality of substantially spherical beads by effect of gravity to a lower track end,
    (b) an enclosure sealingly housing said track, comprising
        a side wall enclosing outer lateral surfaces of said track,
        a cover sealingly enclosing an upper track end of said track and upper end of said side wall, and
        a base including upper and lower sections defining a plunger chamber, and a first bead chamber defined in said upper section communicating with said lower track end and said first bead chamber being offset along said plunger chamber relative to a bead exit opening in said lower section,
    c) a plunger sealingly provided in said plunger chamber and being capable of horizontal reciprocal movement within said plunger chamber, said plunger having a throughhole defining a second bead chamber normally aligned with said first bead chamber at said lower track end and with a plunger portion concurrently blocking said exit opening via a biasing means imposing a normal horizontal bias force on said plunger, wherein when a horizontal force is exerted in opposition to and adequate to overcome said normal horizontal bias force said plunger being capable of horizontal movement to align said second bead chamber with said exit opening, said normal horizontal bias force of said biasing means capable of horizontally moving said plunger effective to reblock said exit opening upon removal of said opposing force, and wherein said plunger further comprises first and second resilient sealing rings, respectively, where said first flange is located between said exit opening and said first bead chamber and said second flange is located between said biasing means and a distal end of said plunger at which said horizontal force is exerted, and (2) identifying means for identifying each of said bead dispenser devices;

(IV) means comprising a rotatable reagent pack carousel for receiving a plurality of reagent storage packs capable of storing and permitting reagent withdrawal, in a self-sealing manner, whereby a plurality of different reagents stored on-board said analyzer can be selected from for addition to said reaction tube for performing a particular assay in said reaction tube, and wherein said reagent pack carousel is located concentrically within said sample tube carousel, and said sample tube carousel, and said inert support pack carousel are independently rotatable relative to each other;

(V) means for pipetting sample and means for pipetting reagent into a support-containing reaction tube at a reaction tube pipetting station;

(VI) an incubating station for incubating reaction tubes received from said reaction tube pipetting station containing sample, reagent and inert support;

(VII) a washing station for washing bound biomaterial in said reaction tube after said reaction tubes have been incubated at said incubating station;

(VIII) a detection station for detecting a quantity of analyte bound to said biomaterial in said reaction tubes after said reaction tubes have been washed at said washing station, said detection station producing a signal proportional to the quantity of analyte for each reaction tube;

(IX) a reaction tube transport pathway connecting, in this sequence, said reaction tube supply means, said inert support supply and dispensing means, said reaction tube pipetting station, said incubating station, said washing station and said detection station;

(X) means for identifying said sample tubes, said reagent storage packs, and said inert support dispensing packs on-board the analyzer;

(XI) control means for automatic controlling of various components of said analyzer in a coordinated manner and being capable of executing assay selection orders for a given sample by selecting and coordinating the introduction of a particular type of reagent and particular type of biomaterial-coated inert support effective to perform a particular requested assay on said sample in a reaction tube; and (XII) means for determining, and displaying and/or recording the concentration of analyte in a particular sample based on said signal produced and detected at said detection station.

* * * * *